United States Patent [19]

Osswald et al.

[11] Patent Number: 5,726,194

[45] Date of Patent: Mar. 10, 1998

[54] ENDOTHELIN RECEPTOR ANTAGONISTS

[75] Inventors: Mathias Osswald, Zwingenberg; Werner Mederski, Erzhauzen; Dieter Dorsch, Ober-Ramstadt; Claudia Wilm, Muhltal; Claus Schmitges, Gross-Umstadt; Maria Christadler, Rodermark, all of Germany

[73] Assignee: Merck Patent Gesellschaft mit beschrankter Haftung, Darmstadt, Germany

[21] Appl. No.: 617,342

[22] Filed: Mar. 18, 1996

[30] Foreign Application Priority Data

Mar. 18, 1995 [DE] Germany ............... 195 09 950.8

[51] Int. Cl.⁶ ............. A61K 31/41; A61K 31/445; C07D 271/12; C07D 285/14
[52] U.S. Cl. ............. 514/362; 514/316; 514/322; 514/364; 546/187; 546/199; 548/126
[58] Field of Search ............. 514/362, 364, 514/322, 316; 546/187, 199; 548/126

[56] References Cited

U.S. PATENT DOCUMENTS 5,378,715 1/1995 Stein et al. ............... 514/329
5,464,853 11/1995 Chan et al. ............... 514/378

FOREIGN PATENT DOCUMENTS 2095174 7/1993 Canada .
9427979 12/1994 WIPO .

OTHER PUBLICATIONS

Inpadoc Abstract Services—U.S. Patent 5,378,715, EP 569, 193 & WO 94279979.
Khaletsky et al., Synthesis of Piazothiole(3,4-Benzo-1,2, 5-Thiodiazole) and Its Derivatives, Journal of General Chemistry, vol. 24 pp. 131–133, 1954.
Pesin et al., Chemistry of Heterocyclic Compounds, Khimiya Geterotsiklicheskikh Soedinenii, vol. 4, No. 5, pp. 587–588, 1968.
Chemical Abstract, vol. 49, No. 5, Abstract No. 3170a.
Chemical Abstract, vol. 71, No. 1, Abstract No. 3332m.

Primary Examiner—Mulund J. Shah
Assistant Examiner—Brenda Coleman
Attorney, Agent, or Firm—Millen, White, Zelano, & Branigan, P.C.

[57] ABSTRACT

Novel compounds of the formula I

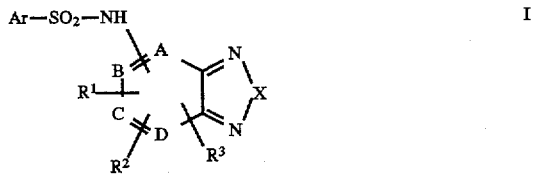

in which $R^1$, $R^2$, $R^3$, —A=B—C=D—, Ar and X have the meaning indicated in claim 1, and their salts show endothelin receptor-antagonistic properties.

13 Claims, No Drawings

ENDOTHELIN RECEPTOR ANTAGONISTS

The invention relates to compounds of the formula I

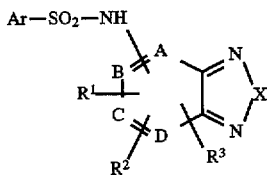  I in which

—A=B—C=D— is a —CH=CH—CH=CH— group in which 1 or 2 CH groups can also be replaced by N, and in which each H group can independently be replaced by $R^1$, $R^2$ or $R^3$, Ar is Ph or naphthyl, which is unsubstituted or mono-, di- or trisubstituted by H, Hal, Q, alkenyl having 2 to 6 C atoms, Ph, OPh, $NO_2$, $NR^4R^5$, $NHCOR^4$, $CF_3$, $OCF_3$, CN, $OR^4$, $COOR^4$, $(CH_2)_nCOOR^4$, $(CH_2)_nNR^4R^5$, —N=C=O or $NHCONR^4R^5$, $R^1$, $R^2$ and $R^3$ in each case independently of one another are absent, H, Hal, Q, $CF_3$, $NO_2$, $NR^4R^5$, CN, $COOR^4$ or $NHCOR^5$, $R^4$ and $R^5$ in each case independently of one another are H or Q, or together are also —$CH_2$—$(CH_2)_n$—$CH_2$—, Q is alkyl having 1 to 6 C atoms, Ph is phenyl, X is O or S, Hal is F, Cl, Br or I, n is 1, 2 or 3, and also their salts, excluding 4-methyl-N-(2,1,3-benzothiadiazol-5-yl)benzene-sulfonamide, 4-nitro-N-(2,1,3-benzothiadiazol-5-yl)-benzenesulfonamide and 4-amino-N-(2,1,3-benzothiadiazol-5-yl-benzenesulfonamide.

BACKGROUND OF THE INVENTION

Similar compounds are disclosed in EP 0 558 258 A1, EP 0 569 193 A1 and WO 94/27979.

4-Methyl-N-(2,1,3-benzothiadiazol-5-yl)benzene-sulfonamide is described in Khim. Geterotsikl. Soedin. (1968), 5, 812–14.

4-Nitro-N-(2,1,3-benzothiadiazol-5-yl)benzenesulfonamide and 4-amino-N-(2,1,3-benzothiadiazol-5-yl) benzenesulfonamide are described in Zh. Obshch. Khim. (1954), 24, 133–136.

No pharmacological actions are described, however, for these compounds.

SUMMARY OF THE INVENTION

An object of the invention is finding novel compounds having useful properties, in particular those which can be used for the production of medicaments.

Upon further study of the specification and appended claims, further objects and advantages of this invention will become apparent to those skilled in the art.

It has been found that the compounds of the formula I and their salts have very useful pharmacological properties together with good tolerability. In particular, they show endothelin receptor-antagonistic properties and can therefore be employed for the treatment of illnesses such as hypertension, cardiac insufficiency, coronary heart disease, renal, cerebral and myocardial ischaemia, renal insufficiency, cerebral infarct, subarachnoid hemorrhage, arteriosclerosis, pulmonary high blood pressure, inflammations, asthma, prostate hyperplasia, endotoxic shock and in the case of complications after the administration of substances such as cyclosporin, and also other illnesses associated with endothelin activities.

The compounds show, inter alia, a high affinity for the endothelin subreceptors $ET_A$ and $ET_B$.

These activities can be determined according to customary in vitro or in vivo methods, such as described by P. D. Stein et al., J. Med. Chem. 37, 1994, 329–331 and E. Ohlstein et al., Proc. Natl. Acad. Sci. U.S.A. 91, 1994, 8052–8056. The hypotensive action M. K. Bazil et al., J. Cardiovasc. Pharmacol. 22, 1993, 897–905 and J. Lange et al., Lab Animal 20, 1991, Appl. Note 1016.

The compounds of the formula I can be employed as pharmaceutically active compounds in human and veterinary medicine, in particular for the prophylaxis and/or therapy of cardiac, circulatory and vascular disorders, especially hypertension and cardiac insufficiency.

The invention relates to the compounds of the formula I and their salts, and to a process for the preparation of these compounds and their salts, characterized in (a) a compound of the formula II

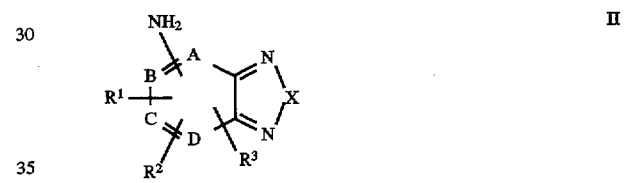  II in which

—A=B—C=D—, $R^1$, $R^2$, $R^3$ and X have the meanings indicated above, is reacted with a compound of the formula III

  III in which

E is Cl, Br, I or a free or reactive functionally modified OH group and

Ar has the meaning indicated above, or (b) in that for the preparation of a compound of the formula I, in which X is S, or the compounds of 4-methyl-N-(2,1,3-benzo-thiadiazol-5-yl)benzenesulfonamide, 4-nitro-N-(2,1,3-benzothiadiazol-5-yl)benzene-sulfonamide or 4-amino-N-(2,1,3-benzothiadiazol-5-yl)benzenesulfonamide, a compound of the formula IV

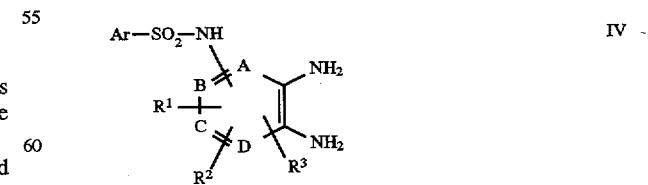  IV in which

—A=B—C=D—, Ar, $R^1$, $R^2$ and $R^3$ have the meanings above, is reacted with thionyl chloride or a reactive derivative of this compound, or c) in that for the preparation of a compound of the formula I, in which X is O, a compound of the formula V

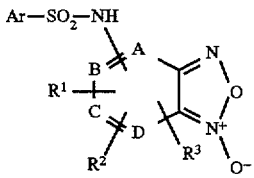

in which

—A=B—C=D—, Ar, $R^1$, $R^2$ and $R^3$ have the meanings indicated above, is reduced, and/or in that in a compound of the formula I one or more radicals $R^1$, $R^2$ and/or $R^3$ are converted into one or more other radicals $R^1$, $R^2$ and/or $R^3$, by i) reducing a nitro group to an amino group,
ii) replacing a bromo substituent by a cyano group,
iii) hydrolyzing a cyano group to a carboxyl group,
iv) esterifying a carboxyl group,
v) converting an amino group by reductive amination into an alkylated amine or
vi) acylating an amino group and/or converting a base or acid of the formula I into one of its salts.

Above and below, the radicals or parameters —A=B—C=D—, Ar, $R^1$ to $R^5$, Q, Ph, X, Hal and n have the meanings indicated under the formulae I to V, if nothing is expressly stated otherwise.

In the above formulae, Q is alkyl having 1 to 6, preferably 1, 2, 3 or 4 C atoms. Q is preferably methyl, furthermore ethyl, propyl, isopropyl, butyl, isobutyl, sec-butyl or tert-butyl, and further also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, or 1,1,2- or 1,2,2-trimethylpropyl.

Alkenyl is preferably vinyl, 1- or 2-propenyl, 1-butenyl, and further 1-pentenyl or 1-hexenyl.

Hal is preferably F, Cl or Br, but also I.

Ar is unsubstituted, preferably monosubstituted, as indicated, phenyl or naphthyl, specifically preferably phenyl, o- or m-tolyl, o-, m- or p-ethyl-phenyl, o-, m- or p-propylphenyl, o-, m- or p-isopropylphenyl, o-, m- or p-tert-butylphenyl, m- or p-trifluoromethylphenyl, o-, m- p-phenylphenyl, o-, m- or p-hydroxyphenyl, o- or m-nitrophenyl, o- or m-aminophenyl, o-, m- or p-methylaminophenyl, o-, m- or p-dimethylaminophenyl, o-, m- or p-acetamidophenyl, o-, m- or p-(trifluoromethoxy)phenyl, o-, m- or p-cyanophenyl, o-, m- or p-(N-pyrrolidino)phenyl, o-, m- or p-(N-piperidino)phenyl, o-, m- or p-methoxyphenyl, o-, m- or p-ethoxyphenyl, o-, m- or p-phenoxyphenyl, o-, m- or p-carboxyphenyl, o-, m- or p-methoxycarbonylphenyl, o-, m- or p-ethoxycarbonylphenyl, o-, m- or p-(carboxymethyl)phenyl, o-, m- or p-(methoxycarbonylmethyl)phenyl, o-, m- or p-(methoxycarbonylethyl)phenyl, o-, m- or p-(aminomethyl)phenyl, o-, m- or p-(N-methylaminomethyl)phenyl, o-, m- or p-(N,N-dimethylamino)phenyl, o-, m- or p-(N-ethylamino)phenyl, o-, m- or p-(N,N-diethylamino)phenyl, o-, m- or p-(N,N-dimethylaminomethyl)phenyl, o-, m- or p-(N-pyrrolidinomethyl)phenyl, o-, m- or p-(N-piperidinomethyl)phenyl, o-, m- or p-isocyanatophenyl, o-, m- or p-carbamidophenyl, o-, m- or p-(N-methylcarbamoyl)phenyl, o-, m- or p-(N,N-dimethylcarbamoyl)phenyl, o-, m- or p-fluorophenyl, o-, m- or p-bromophenyl, o-, m- or p-chlorophenyl, further preferably naphthyl, 5-methylnaphthyl, 5-ethylnaphthyl, 5-propylnaphthyl, 5-isopropylnaphthyl, 5-tert-butylnaphthyl, 5-trifluoromethylnaphthyl, 5-phenylnaphthyl, 5-hydroxynaphthyl, 5-nitronaphthyl, 5-aminonaphthyl, 5-N-methylaminonaphthyl, 5-N,N-dimethylaminonaphthyl, 5-acetamidonaphthyl, 5-(trifluoromethoxy)naphthyl, 5-cyanonaphthyl, 5-(N-pyrrolidino)naphthyl, 5-(N-piperidino)naphthyl, 5-methoxynaphthyl, 5-ethoxynaphthyl, 5-carboxynaphthyl, 5-methoxycarbonylnaphthyl, 5-ethoxycarbonylnaphthyl, 5-(carboxymethyl)naphthyl, 5-(methoxycarbonylmethyl)naphthyl, 5-(ethoxycarbonylmethyl)naphthyl, 5-(aminomethyl)naphthyl, 5-(N-methylaminomethyl)naphthyl, 5-(N,N-dimethylaminomethyl)naphthyl, 5-N-ethylaminonaphthyl, 5-(N,N-diethylamino)naphthyl, 5-(N-pyrrolidinomethyl)naphthyl, 5-(N-piperidinomethyl)naphthyl, 5-isocyanatonaphthyl, 5-carbamidonaphthyl, 5-(N-methylcarbamoyl)naphthyl, 5-(N,N-dimethylcarbamoyl)naphthyl, 5-N-isopropylaminonaphthyl, 5-N-isopropyl-N-methylaminonaphthyl, 5-fluoronaphthyl, 5-chloronaphthyl, 5-bromonaphthyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl, 2-chloro-4-methyl, 2-chloro-5-methyl, 2-chloro-6-methyl, 2-methyl-3chloro, 2-methyl-4-chloro, 2-methyl-5-chloro, 2-methyl-6-chloro, 3-chloro-4-methyl, 3-chloro-5-methyl or 3-methyl-4-chlorophenyl, 2-bromo-3-methyl, 2-bromo-4-methyl, 2-bromo-5-methyl, 2-bromo-6-methyl, 2-methyl-3-bromo, 2-methyl-4-bromo, 2-methyl-5-bromo, 2-methyl-6-bromo, 3-bromo-4-methyl, 3-bromo-5-methyl or 3-methyl-4-bromophenyl, 2,4- or 2,5-dinitrophenyl, 2,5- or 3,4-dimethoxyphenyl, 3-nitro-4-chlorophenyl, 2-amino-3-chloro, 2-amino-4-chloro, 2-amino-5-chloro or 2-amino-6-chlorophenyl, 2-nitro-4-N,N-dimethylamino or 3-nitro-4-N,N-dimethylaminophenyl, 3-carboxy-2-methoxy, 3-carboxy-4-methoxy or 3-carboxy-5-methoxyphenyl, 2,3,4-, 2,3,5-, 2,3,6-, 2,4,6- or 3,4,5-trichlorophenyl, 2,4,6-tri-tert-butylphenyl, further preferably 2-nitro-4-(trifluoromethyl)phenyl, 3,5-di-(trifluoromethyl)phenyl, 2,5-dimethylphenyl, 2-hydroxy-3,5-dichlorophenyl, 2-fluoro-5- or 4-fluoro-3-(trifluoromethyl)phenyl, 4-chloro-2- or 4-chloro-3-(trifluoromethyl), 2-chloro-4- or 2-chloro-5-(trifluoromethyl)phenyl, 4-bromo-2- or 4-bromo-3-(trifluoromethyl)phenyl, p-iodophenyl, p-vinylphenyl, 5-(N, N-dibutylamino)naphthyl, 2-nitro-4-methoxyphenyl, 2,5-dimethoxy-4-nitrophenyl, 3,5-dicarboxyphenyl, 2-chloro-3-nitro-5-carboxyphenyl, 4-chloro-3-carboxyphenyl, 2-methyl-5-nitrophenyl, 2,4-dimethyl-3-nitrophenyl, 3,6-dichloro-4-aminophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 3-chloro-4-acetamidophenyl, 4-hydroxy-3-carboxyphenyl, 2-methoxy-5-methylphenyl or 2,4,6-triisopropylphenyl.

The radical —A=B—C=D— is preferably —CH=CH—CH=N—, and further —CH=N—CH=CH— or —CH=N—CH=N—, but particularly preferably —CH=CH—CH=CH—.

The radicals $R^1$, $R^2$ and $R^3$ are in each case independently of one another preferably H, Q, in particular $CH_3$, Hal, in particular chlorine or bromine, but further also preferably $NO_2$ or $CF_3$.

The parameter n is preferably 0 or 1, and further preferably 2.

The compounds of the formula I can have one or more chiral centers and therefore occur in various stereoisomeric forms. The invention includes all these forms.

Accordingly, the invention relates in particular to those compounds of the formula I in which at least one of the radicals mentioned has one of the preferred meanings indicated above. Some preferred groups of compounds can be expressed by the following subformulae Ia to Ig which correspond to the formula I and in which the radicals which are not described in greater detail have the meaning indicated under the formula I, but in which in Ia X is S;

in Ib X is O;

in Ic X is S and
—A=B—C=D— is —CH=CH—CH=CH—;

in Id X is O and
—A=B—C=D— is —CH=CH—CH=CH—;

in Ie X is O and
—A=B—C=D— is —CH=CH—CH=N—;

in If X is S,
—A=B—C=D— is —CH=CH—CH=CH—,
$R^1$ is H,
$R^2$ is Hal and
$R^3$ is methyl;

in Ig Ar is 5-(N,N-dimethylamino)naphthyl.

The compounds of the formula I and also the starting substances for their preparation are otherwise prepared by methods known per se, as are described in the literature (e.g. in the standard works such as Houben-Weyl, Methoden der organischen Chemie (Methods of Organic Chemistry), Georg-Thieme-Verlag, Stuttgart; but in particular in EP 0569 193 A and WO 94/27979), namely under reaction conditions which are known and suitable for the reactions mentioned. In this case use can also be made of variants which are known per se but not mentioned here in greater detail.

The starting substances can, if desired, also be formed in situ, such that they are not isolated from the reaction mixture, but immediately reacted further to give the compounds of the formula I.

The compounds of the formula I can preferably be obtained by reacting compounds of the formula II with compounds of the formula III.

In the compounds of the formula III, E is preferably Cl, Br, I or a reactive modified OH group such as alkylsulfonyloxy having 1–6 C atoms (preferably methylsulfonyloxy) or arylsulfonyloxy having 6–10 C atoms (preferably phenyl- or p-tolylsulfonyloxy).

The reaction is performed, in general, in an inert solvent in the presence of one or more bases, preferably of a tertiary amine, e.g. triethylamine, pyridine, 4-dimethylaminopyridine, expediently at temperatures between 0° and 150° C., preferably between 40° and 90° C. An excess of the amine can also be used as a solvent.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

The starting compounds of the formula II are generally novel. However, they can be prepared by methods which are known per se. For example, 5-amino-6-methyl-2,1,3-benzothiadiazole can thus be prepared from 5-nitro-6-methyl-2,1,3-benzothiadiazole by hydrogenation on Raney Nickel in an inert solvent such as methanol. This is expediently carried out at temperatures between 0° and approximately 200° C. preferably between 30° and 80° C.

Compounds of the formula I in which X is S can furthermore be obtained by reacting compounds of the formula IV, which are generally novel, with thionyl chloride or a reactive derivative of this compound such as thionylaniline, analogously to known processes, as are described in the literature (e.g. J. Heterocycl. Chem. 7, 629 (1970)), in an inert solvent in the presence of one or more bases, preferably of a tertiary amine, e.g. triethylamine, pyridine, 4-dimethylaminopyridine, expediently at temperatures between 0° and 150° C., preferably between 40° and 90° C. An excess of the amine can also be used as a solvent.

Compounds of the formula I in which X is O can furthermore be obtained by reacting compounds of the formula V, which are generally novel, with reducing compounds such as Cl—$SO_2$—N=C=O, $POCl_3$, $PCl_3$, $Na_2S_2O_4$, $Ph_3P$ or $P(OC_2H_5)_3$ analogously to known processes, as are described in the literature (e.g. Tetrahedron 44, 5209 (1988), Tetrahedron 48, 8199 (1992), Z. Chem. 20, 257 (1980), J. Org. Chem. 47, 1774 (1982), J. Org. Chem. 28, 1656 (1963) or J. Med. Chem. 11, 305 (1968)).

The starting compounds of the formula V can be prepared by methods which are known per se. For example, 4-tert-butyl-N-(2,1,3-benzoxadiazole-1-N-oxid-5yl) benzenesulfonamide can thus be prepared from 4-tert-butyl-N-(4-chloro-3-nitro)benzenesulfonamide by reaction with sodium azide under phase-transfer catalysis via 4-tert-butyl-N-(4-azido-3-nitro)benzenesulfonamide and subsequent cyclization in glacial acetic acid.

It is further possible to convert a compound of the formula I into another compound of the formula I by converting one or more radicals $R^1$, $R^2$ and/or $R^3$ into one or more other radicals $R^1$, $R^2$ and/or $R^3$, e.g. by reducing nitro groups, for example by hydrogenation on Raney Nickel or Pd-carbon in an inert solvent such as methanol or ethanol, to amino groups and/or converting bromo substituents by reaction with, for example, copper (I) cyanide into cyano groups and/or hydrolyzing cyano groups to COOH groups and/or esterifying carboxyl groups by reaction with alcohols and/or alkylating nitro groups under hydrogenolytic conditions, alkylated amines being obtained.

Free amino groups can further be acylated in a customary manner using an acid chloride or anhydride or alkylated using an unsubstituted or substituted alkyl halide, expediently in an inert solvent such as dichloromethane or THF and/or in the presence of a base such as triethylamine or pyridine at temperatures between –60° and +30° C.

If desired, a functionally modified amino and/or hydroxyl group in a compound of the formula I can be liberated by solvolysis or hydrogenolysis according to customary methods. For example, a compound of the formula I which contains an $NHCOR^4$ or a $COOR^4$ group can thus be converted into the corresponding compound of the formula I which, instead of this, contains an $NH_2$ or a COOH group. $COOR^4$ groups can be hydrolyzed, for example, using NaOH or KOH in water, water-THF or water-dioxane at temperatures between 0° and 100° C.

A base of the formula I can be converted with an acid to the associated acid addition salt, for example by reaction of equivalent amounts of the base and of the acid in an inert solvent such as ethanol and subsequent evaporation. For this reaction, in particular, possible acids are those which yield physiologically acceptable salts. Inorganic acids can thus be used, e.g. sulfuric acid, nitric acid, halohydric acids such as hydrochloric acid or hydrobromic acid, phosphoric acids such as orthophosphoric acid, sulfamic acid, and also organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or carbonate) into the corresponding metal salts, in particular alkali metal or alkaline-earth metal salts, or into the corresponding ammonium salts.

The invention further relates to the use of the compounds of the formula I and/or 4-methyl-N-(2,1,3-benzothiadiazol-5-yl)benzenesulfonamide and/or 4-nitro-N-(2,1,3-benzothiadiazol-5-yl)benzenesulfonamide and/or 4-amino-N-(2,1,3-benzothiadiazol-5-yl)benzenesulfonamide and/or their physiologically acceptable salts for the production of pharmaceutical preparations, in particular by non-chemical routes. In this context, they can be brought into a suitable dose form together with at least one solid, liquid and/or semi-liquid excipient or auxiliary and, if appropriate, in combination with one or more further active compounds.

The invention further relates to pharmaceutical preparations comprising at least one compound of the formula I and/or 4-methyl-N-(2,1,3-benzothiadiazol-5-yl) benzenesulfonamide and/or 4-nitro-N-(2,1,3-benzothiadiazol-5-yl)benzenesulfonamide and/or 4-amino-N-(2,1,3-benzothiadiazol-5-yl)benzenesulfonamide and/or one of their physiologically acceptable salts.

These preparations can be used as medicaments in human or veterinary medicine. Possible excipients are organic or inorganic substances which are suitable for enteral (e.g. oral) or parenteral administration or topical application and do not react with the active compounds, for example water, vegetable oils, benzyl alcohols, alkylene glycols, polyethylene glycols, glycerol triacetate, gelatin, carbohydrates such as lactose or starch, magnesium stearate, talc and petroleum jelly. In particular, tablets, pills, coated tablets, capsules, powders, granules, syrups, juices or drops are used for oral administration, suppositories are used for rectal administration, solutions, preferably oily or aqueous solutions, and further suspensions, emulsions or implants, are used for parenteral administration and ointments, creams or powders are used for topical application. The novel compounds can also be lyophilized and the lyophilizates obtained, used, for example, for the production of injection preparations. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or aromatic substances. They can also contain, if desired, one or more other active compounds, e..g. one or more vitamins.

The compounds of the formula I and their physiologically acceptable salts can be used as described above, such as in the control of disorders, in particular of hypertension and cardiac insufficiency.

The compounds may be administered in doses similar to those known for ACE inhibitors, such as captopril or enalapril.

In this context, the substances according to the invention are generically preferably administered in doses of from approximately 1 to 500 mg, in particular from 5 to 100 mg per dose unit. The daily dose is preferably from approximately 0.02 to 10 mg/kg of body weight. The specific dose for any patient depends, however, on all sorts of factors, for example on the activity of the specific compound employed, on the age, body weight, general state of health, sex, on the diet, on the time and route of administration, on the excretion rate, pharmaceutical substance combination and severity of the particular disease to which the therapy applies. Oral administration is preferred.

Above and below, all temperatures are indicated in °C. In the following examples, "customary working up" means: water is added, if necessary, the mixture is adjusted, if necessary, depending on the constitution of the final product, to pHs of from 2 to 10, and extracted with ethyl acetate or dichloromethane, the solid is separated off, and the organic phase is dried over sodium sulfate, evaporated and purified by chromatography on silica gel and/or by crystallization. $R_f$ values on silica gel; eluent: ethyl acetate/methanol 9:1.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. DE 195 09 950.8, filed Mar. 18, 1995, are hereby incorporated by reference.

EXAMPLES

Example 1

A solution of 3 g of 5-dimethylaminonaphthalenesulfonylchloride ("A") in 10 ml of pyridine is added to a solution of 1.53 g of 5-amino-2,1,3-benzothiadiazole, obtainable by hydrogenation of 5-nitro-2,1,3-benzothiadiazole on Raney Nickel in methanol, in 15 ml of pyridine, and the mixture is stirred for 24 hours at 60°, then added to 75 ml of 2N hydrochloric acid and worked up in the customary manner. 5-Dimethylamino-N-(2,1,3-benzothiadiazol-5-yl)-1-naphthalenesulfonamide is obtained as a yellow solid, m.p. 73°, potassium salt, m.p.>300°.

Analogously, from the following mZ-5-amino-2,1,3-benzothiadiazoles, in which mZ is 4-methyl
6-methyl
7-methyl
4,6-dimethyl
4,7-dimethyl
6,7-dimethyl
4-trifluoromethyl 6-trifluoromethyl
7-trifluoromethyl
4-bromo
6-bromo
7-bromo
4,6-dibromo
4,7-dibromo
6,7-dibromo
4-bromo-6-methyl
4-bromo-7-methyl
6-bromo-7-methyl
4-methyl-6-bromo
4-methyl-7-bromo
6-methyl-7-bromo
4-bromo-6-ethyl
4-bromo-7-ethyl
6-bromo-7-ethyl
4-ethyl-6-bromo
4-ethyl-7-bromo
6-ethyl-7-bromo
4-bromo-6-trifluoromethyl
4-bromo-7-trifluoromethyl
6-bromo-7-trifluoromethyl
4-trifluoromethyl-6-bromo
4-trifluoromethyl-7-bromo
6-trifluoromethyl-7-bromo
4-chloro
6-chloro
7-chloro
4-nitro
6-nitro
7-nitro
4-bromo-6-tert-butyl
4-bromo-7-tert-butyl
6-bromo-7-tert-butyl
4-tert-butyl-6-bromo
4-tert-butyl-7-bromo
6-tert-butyl-7-bromo
4-chloro-6-methyl
4-chloro-7-methyl
6-chloro-7-methyl
4-methyl-6-chloro
4-methyl-7-chloro
6-methyl-7-chloro
4-dimethylamino
6-dimethylamino
7-dimethylamino
4-cyano
6-cyano
7-cyano
4-methoxycarbonyl
6-methoxycarbonyl
7-methoxycarbonyl
4-ethoxycarbonyl
6-ethoxycarbonyl
7-ethoxycarbonyl
4-acetamido
6-acetamido and
7-acetamido,
with "A", the 5-dimethylamino-mZ-1-naphthalenesulfonamides below are obtained, in which mZ is N-(4-methyl-2,1,3-benzothiadiazol-5-yl), m.p. 159°
N-(6-methyl-2,1,3-benzothiadiazol-5-yl)
N-(7-methyl-2,1,3-benzothiadiazol-5-yl)
N-(4,6-dimethyl-2,1,3-benzothiadiazol-5-yl)
N-(4,7-dimethyl-2,1,3-benzothiadiazol-5-yl)
N-(6,7-dimethyl-2,1,3-benzothiadiazol-5-yl)
N-(4-trifluoromethyl-2,1,3-benzothiadiazol-5-yl)
N-(6-trifluoromethyl-2,1,3-benzothiadiazol-5-yl)
N-(7-trifluoromethyl-2,1,3-benzothiadiazol-5-yl)
N-(4-bromo-2,1,3-benzothiadiazol-5-yl), m.p. 151°
N-(6-bromo-2,1,3-benzothiadiazol-5-yl)
N-(7-bromo-2,1,3-benzothiadiazol-5-yl)
N-(4,6-dibromo-2,1,3-benzothiadiazol-5-yl)
N-(4,7-dibromo-2,1,3-benzothiadiazol-5-yl)
N-(6,7-dibromo-2,1,3-benzothiadiazol-5-yl)
N-(4-bromo-6-methyl-2,1,3-benzothiadiazol-5-yl)
N-(4-bromo-7-methyl-2,1,3-benzothiadiazol-5-yl)
N-(6-bromo-7-methyl-2,1,3-benzothiadiazol-5-yl)
N-(4-methyl-6-bromo-2,1,3-benzothiadiazol-5-yl)
N-(4-methyl-7-bromo-2,1,3-benzothiadiazol-5-yl)
N-(6-methyl-7-bromo-2,1,3-benzothiadiazol-5-yl)
N-(4-bromo-6-ethyl-2,1,3-benzothiadiazol-5-yl)
N-(4-bromo-7-ethyl-2,1,3-benzothiadiazol-5-yl)
N-(6-bromo-7-ethyl-2,1,3-benzothiadiazol-5-yl)
N-(4-ethyl-6-bromo-2,1,3-benzothiadiazol-5-yl)
N-(4-ethyl-7-bromo-2,1,3-benzothiadiazol-5-yl)
N-(6-ethyl-7-bromo-2,1,3-benzothiadiazol-5-yl)
N-(4-bromo-6-trifluoromethyl-2,1,3-benzothiadiazol-5-yl)
N-(4-bromo-7-trifluoromethyl-2,1,3-benzothiadiazol-5-yl)
N-(6-bromo-7-trifluoromethyl-2,1,3-benzothiadiazol-5-yl)
N-(4-trifluoromethyl-6-bromo-2,1,3-benzothiadiazol-5-yl)
N-(4-trifluoromethyl-7-bromo-2,1,3-benzothiadiazol-5-yl)
N-(6-trifluoromethyl-7-bromo-2,1,3-benzothiadiazol-5-yl)
N-(4-chloro-2,1,3-benzothiadiazol-5-yl), m.p. 168°
N-(6-chloro-2,1,3-benzothiadiazol-5-yl)
N-(7-chloro-2,1,3-benzothiadiazol-5-yl)
N-(4-nitro-2,1,3-benzothiadiazol-5-yl)
N-(6-nitro-2,1,3-benzothiadiazol-5-yl)
N-(7-nitro-2,1,3-benzothiadiazol-5-yl)
N-(4-bromo-6-tert-butyl-2,1,3-benzothiadiazol-5-yl)
N-(4-bromo-7-tert-butyl-2,1,3-benzothiadiazol-5-yl)
N-(6-bromo-7-tert-butyl-2,1,3-benzothiadiazol-5-yl)
N-(4-tert-butyl-6-bromo-2,1,3-benzothiadiazol-5-yl)
N-(4-tert-butyl-7-bromo-2,1,3-benzothiadiazol-5-yl)
N-(6-tert-butyl-7-bromo-2,1,3-benzothiadiazol-5-yl)
N-(4-chloro-6-methyl-2,1,3-benzothiadiazol-5-yl)
N-(4-chloro-7-methyl-2,1,3-benzothiadiazol-5-yl)
N-(6-chloro-7-methyl-2,1,3-benzothiadiazol-5-yl)
N-(4-methyl-6-chloro-2,1,3-benzothiadiazol-5-yl)
N-(4-methyl-7-chloro-2,1,3-benzothiadiazol-5-yl)
N-(6-methyl-7-chloro-2,1,3-benzothiadiazol-5-yl)
N-(4-dimethylamino-2,1,3-benzothiadiazol-5-yl)
(6-dimethylamino2,1,3-benzothiadiazol-5-yl)
N-(7-dimethylamino-2,1,3-benzothiadiazol-5-yl)
N-(4-cyano-2,1,3-benzothiadiazol-5-yl)
N-(6-cyano-2,1,3-benzothiadiazol-5-yl)
N-(7-cyano-2,1,3-benzothiadiazol-5-yl)
N-(4-methoxycarbonyl-2,1,3-benzothiadiazol-5-yl)
N-(6-methoxycarbonyl-2,1,3-benzothiadiazol-5-yl)
N-(7-methoxycarbonyl-2,1,3-benzothiadiazol-5-yl)
N-(4-ethoxycarbonyl-2,1,3-benzothiadiazol-5-yl)
N-(6-ethoxycarbonyl-2,1,3-benzothiadiazol-5-yl)
N-(7-ethoxycarbonyl-2,1,3-benzothiadiazol-5-yl)
N-(4-acetamido-2,1,3-benzothiadiazol-5-yl)
N-(6-acetamido-2,1,3-benzothiadiazol-5-yl)
N-(7-acetamido-2,1,3-benzothiadiazol-5-yl).

Analogously, by reaction of 4-amino-2,1,3-benzothiadiazole with "A", 5-dimethylamino-N-(2,1,3-benzothiadiazol-4-yl)-1-naphthalene sulfonamide, m.p. 81°, is obtained and from the following 4-amino-mZ-2,1,3-benzothiadiazoles, in which mZ is 5-methyl
6-methyl
7-methyl
5,6-dimethyl
5,7-dimethyl
6,7-dimethyl
5-trifluoromethyl
6-trifluoromethyl
7-trifluoromethyl
5-bromo
6-bromo
7-bromo
5,6-dibromo
5,7-dibromo
6,7-dibromo
5-bromo-6-methyl
5-bromo-7-methyl
6-bromo-7-methyl
5-methyl-6-bromo
5-methyl-7-bromo
6-methyl-7-bromo
5-bromo-6-ethyl
5-bromo-7-ethyl
6-bromo-7-ethyl
5-ethyl-6-bromo
5-ethyl-7-bromo
6-ethyl-7-bromo
5-bromo-6-trifluoromethyl
5-bromo-7-trifluoromethyl
6-bromo-7-trifluoromethyl
5-trifluoromethyl-6-bromo
5-trifluoromethyl-7-bromo
6-trifluoromethyl-7-bromo
5-chloro
6-chloro
7-chloro
5-nitro
6-nitro
7-nitro
5-bromo-6-tert-butyl
5-bromo-7-tert-butyl
6-bromo-7-tert-butyl
5-tert-butyl-6-bromo
5-tert-butyl-7-bromo
5-tert-butyl-7-bromo
5-chloro-6-methyl
5-chloro-7-methyl
6-chloro-7-methyl
5-methyl-6-chloro
5-methyl-7-chloro
6-methyl-7-chloro
5-dimethylamino
6-dimethylamino
7-dimethylamino
5-cyano
6-cyano
7-cyano
5-methoxycarbonyl
6-methoxycarbonyl
7-methoxycarbonyl
5-ethoxycarbonyl
6-ethoxycarbonyl
7-ethoxycarbonyl
5-acetamino
6-acetamido
7-acetamido with "A", the 5-dimethylamino-mZ-1-naphthalenesulfonamides below are obtained, in which mZ is N-(5-methyl-2,1,3-benzothiadiazol-4-yl), m.p. 154°
N-(6-methyl-2,1,3-benzothiadiazol-4-yl)
N-(7-methyl-2,1,3-benzothiadiazol-4-yl), m.p. 170°
N-(5,6-dimethyl-2,1,3-benzothiadiazol-4-yl)
N-(5,7-dimethyl-2,1,3-benzothiadiazol-4-yl)
N-(6,7-dimethyl-2,1,3-benzothiadiazol-4-yl), m.p. 182°
N-(5-trifluoromethyl-2,1,3-benzothiadiazol-4-yl)
N-(6-trifluoromethyl-2,1,3-benzothiadiazol-4-yl)
N-(7-trifluoromethyl-2,1,3-benzothiadiazol-4-yl)
N-(5-bromo-2,1,3-benzothiadiazol-4-yl)
N-(6-bromo-2,1,3-benzothiadiazol-4-yl)
N-(7-bromo-2,1,3-benzothiadiazol-4-yl)
N-(5,6-dibromo-2,1,3-benzothiadiazol-4-yl)
N-(5,7-dibromo-2,1,3-benzothiadiazol-4-yl)
N-(6,7-dibromo-2,1,3-benzothiadiazol-4-yl)
N-(5-bromo-6-methyl-2,1,3-benzothiadiazol-4-yl)
N-(5-bromo-7-methyl-2,1,3-benzothiadiazol-4-yl)
N-(6-bromo-7-methyl-2,1,3-benzothiadiazol-4-yl)
N-(5-methyl-6-bromo-2,1,3-benzothiadiazol-4-yl)
N-(5-methyl-7-bromo-2,1,3-benzothiadiazol-4-yl)
N-(6-methyl-7-bromo-2,1,3-benzothiadiazol-4-yl)
N-(5-bromo-6-ethyl-2,1,3-benzothiadiazol-4-yl)
N-(5-bromo-7-ethyl-2,1,3-benzothiadiazol-4-yl)
N-(6-bromo-7-ethyl-2,1,3-benzothiadiazol-4-yl)
N-(5-ethyl-6-bromo-2,1,3-benzothiadiazol-4-yl)
N-(5-ethyl-7-bromo-2,1,3-benzothiadiazol-4-yl)
N-(6-ethyl-7-bromo-2,1,3-benzothiadiazol-4-yl)
N-(5-bromo-6-trifluoromethyl-2,1,3-benzothiadiazol-4-yl)
N-(5-bromo-7-trifluoromethyl-2,1,3-benzothiadiazol-4-yl)
N-(6-bromo-7-trifluoromethyl-2,1,3-benzothiadiazol-4-yl)
N-(5-trifluoromethyl-6-bromo-2,1,3-benzothiadiazol-4-yl)
N-(5-trifluoromethyl-7-bromo-2,1,3-benzothiadiazol-4-yl)
N-(6-trifluoromethyl-7-bromo-2,1,3-benzothiadiazol-4-yl)
N-(5-chloro-2,1,3-benzothiadiazol-4-yl)
N-(6-chloro-2,1,3-benzothiadiazol-4-yl)
N-(7-chloro-2,1,3-benzothiadiazol-4-yl)
N-(5-nitro-2,1,3-benzothiadiazol-4-yl)
N-(6-nitro-2,1,3-benzothiadiazol-4-yl)
N-(7-nitro-2,1,3-benzothiadiazol-4-yl)
N-(5-bromo-6-tert-butyl-2,1,3-benzothiadiazol-4-yl)
N-(5-bromo-7-tert-butyl-2,1,3-benzothiadiazol-4-yl)
N-(6-bromo-7-tert-butyl-2,1,3-benzothiadiazol-4-yl)
N-(5-tert-butyl-6-bromo-2,1,3-benzothiadiazol-4-yl)
N-(5-tert-butyl-7-bromo-2,1,3-benzothiadiazol-4-yl)
N-(6-tert-butyl-7-bromo-2,1,3-benzothiadiazol-4-yl)
N-(5-chloro-6-methyl-2,1,3-benzothiadiazol-4-yl)
N-(5-chloro-7-methyl-2,1,3-benzothiadiazol-4-yl)
N-(6-chloro-7-methyl-2,1,3-benzothiadiazol-4-yl), m.p. 170°
N-(5-methyl-6-chloro-2,1,3-benzothiadiazol-4-yl)
N-(5-methyl-7-chloro-2,1,3-benzothiadiazol-4-yl)
N-(6-methyl-7-chloro-2,1,3-benzothiadiazol-4-yl)
N-(5-dimethylamino-2,1,3-benzothiadiazol-4-yl)
N-(6-dimethylamino-2,1,3-benzothiadiazol-4-yl)
N-(7-dimethylamino-2,1,3-benzothiadiazol-4-yl)
N-(5-cyano-2,1,3-benzothiadiazol-4-yl)
N-(6-cyano-2,1,3-benzothiadiazol-4-yl)
N-(7-cyano-2,1,3-benzothiadiazol-4-yl)
N-(5-methoxycarbonyl-2,1,3-benzothiadiazol-4-yl)
N-(6-methoxycarbonyl-2,1,3-benzothiadiazol-4-yl)
N-(7-methoxycarbonyl-2,1,3-benzothiadiazol-4-yl)
N-(5-ethoxycarbonyl-2,1,3-benzothiadiazol-4-yl)
N-(6-ethoxycarbonyl-2,1,3-benzothiadiazol-4-yl)

N-(7-ethoxycarbonyl-2,1,3-benzothiadiazol-4-yl)
N-(5-acetamido-2,1,3-benzothiadiazol-4-yl)
N-(6-acetamido-2,1,3-benzothiadiazol-4-yl)
N-(7-acetamido-2,1,3-benzothiadiazol-4-yl).

Example 2

A solution of 3 g of thionyl chloride in 15 ml of toluene is added to a solution of 3.01 g of 4-tert-butyl-N-(1,2-diamino-4-phenyl)-1-benzenesulfonamide and 4.1 g of triethylamine in 100 ml of toluene, the mixture is heated for one hour at 110°, worked up in the customary manner and 4-tert-butyl-N-(2,1,3-benzothiadiazol-5-yl)-1-benzenesulfonamide, m.p. 198°, is obtained.

Analogously, by reaction of N-(1,2-diamino-4-phenyl)-1-benzenesutfonamide with thionyl chloride, N-(2,1,3-benzothiadiazol-5-yl)-1-benzenesulfonamide is obtained and by analogous reaction of the following N-(1,2-diamino-4-phenyl)-mZ-1-benzenesulfonamides, in which mZ is 4-fluoro
4-chloro
4-bromo
4-iodo
4-ethyl
4-propyl
4-isopropyl
3,4-dimethyl
2,5-dimethyl
2,5-diethyl
2,4-diethyl
2,5-dipropyl
3-acetamido
4-acetamido
2-cyano
3-carboxy
2-trifluoromethoxy
3-nitro
4-nitro
2-nitro-5-methyl
2-methyl-5-nitro
2-ethyl-5-nitro
2,4,6-trimethyl
2,4-dichloro
2,5-dichloro
3,4-dichloro
3,5-dichloro
5-bromo-2-methoxy
5-bromo-2-methyl
5-bromo-2-ethyl
5-bromo-2-propyl
2,5-difluoro
3,6-difluoro
2,5-dimethoxy
3,4-dimethoxy
3-trifluoromethyl
4-trifluoromethyl
3,5-di-(trifluoromethyl)
2,4,5-trichloro
2-chloro-4-fluoro
3-chloro-5-fluoro
2-chloro-5-methyl
3-chloro-2-methyl
5-chloro-2-methoxy
2-butyl-5-bromo
2-bromo-5-butyl
2-bromo-5-propyl
5-fluoro-2-methyl
2-phenyl
4-tolyl
2-bromo-5-ethyl with thionyl chloride, the N-(2,1,3-benzothiadiazol-5-yl)-mZ-1-benzenesulfonamides below are obtained in which mZ is 4-fluoro
4-chloro
4-bromo, m.p. 195°
4-iodo
4-ethyl
4-propyl
4-isopropyl
3,4-dimethyl
2,5-dimethyl
2,5-diethyl
2,4-diethyl
2,5-dipropyl
3-acetamido
4-acetamido
2-cyano
3-carboxy
2-trifluoromethoxy
3-nitro
4-nitro
4-nitro-5-methyl
2-methyl-5-nitro
2-ethyl-5-nitro
2,4,6-trimethyl
2,4-dichloro
2,5-dichloro
3,4-dichloro
3,5-dichloro
5-bromo-2-methoxy
5-bromo-2-methyl, m.p. 185°
5-bromo-2-ethyl
5-bromo-2-propyl, m.p. 182°
2,5-difluoro
3,6-difluoro
2,5-dimethoxy
3,4-dimethoxy
3-trifluoromethyl
4-trifluoromethyl
3,5-di-(trifluoromethyl)
2,4,5-trichloro
2-chloro-4-fluoro
3-chloro-5-fluoro
2-chloro-5-methyl
3-chloro-2-methyl
5-chloro-2-methoxy
2-butyl-5-bromo
2-bromo-5-butyl
2-bromo-5-propyl, m.p. 299°
5-fluoro-2-methyl
2-phenyl, m.p. 175°
4-tolyl, m.p. 220°
2-bromo-5-ethyl, m.p. 183°

Example 3

A solution of 1 g of 5-dimethylamino-N-(2,1,3-benzoxadiazol-5-yl-1- or -3-N-oxide)-1-naphthalenesulfonamide (obtainable by heating 5-dimethylamino-N-(1-azido-2-nitro-4-phenyl)-1-naphthalenesulfonamide in glacial acetic acid) and 5 ml of triethyl phosphite in 50 ml of absolute ethanol is heated for 30 minutes at 75°. After removal of the solvent and customary working up, 5-dimethylamino-N-(2,1,3-benzoxadiazol-5-yl)-1-naphthalenesulfonamide, m.p. 106°, is obtained.

Analogously, by reaction of the following 5-dimethylamino-mZ-1-naphthalenesulfonamides in which mZ is N-(4-methyl-2,1,3-benzoxadiazol-5-yl-1- or 3-N-oxide)
N-(6-methyl-2,1,3-benzoxadiazol-5-yl-1- or 3-N-oxide)
N-(7-methyl-2,1,3-benzoxadiazol-5-yl-1- or 3-N-oxide)
N-(4,6-dimethyl-2,1,3-benzoxadiazol-5-yl-1- or 3-N-oxide)
N-(4,7-dimethyl-2,1,3-benzoxadiazol-5-yl-1- or 3-N-oxide)
N-(6,7-dimethyl-2,1,3-benzoxadiazol-5-yl-1- or 3-N-oxide)
N-(4-trifluoromethyl-2,1,3-benzoxadiazol-5-yl-1- or 3-N-oxide)
N-(6-trifluoromethyl-2,1,3-benzoxadiazol-5-yl-1- or 3-N-oxide)
N-(7-trifluoromethyl-2,1,3-benzoxadiazol-5-yl-1- or 3-N-oxide)
N-(4-bromo-2,1,3-benzoxadiazol-5-yl-1- or 3-N-oxide)
N-(6-bromo-2,1,3-benzoxadiazol-5-yl-1- or 3-N-oxide)
N-(7-bromo-2,1,3-benzoxadiazol-5-yl-1- or 3-N-oxide)
N-(4,6-dibromo-2,1,3-benzoxadiazol-5-yl-1- or 3-N-oxide)
N-(4,7-dibromo-2,1,3-benzoxadiazol-5-yl-1- or 3-N-oxide)
N-(6,7-dibromo-2,1,3-benzoxadiazol-5-yl-1- or 3-N-oxide)
N-(4-bromo-6-methyl-2,1,3-benzoxadiazol-5-yl-1- or 3-N-oxide)
N-(4-bromo-7-methyl-2,1,3-benzoxadiazol-5-yl-1- or 3-N-oxide)
N-(6-bromo-7-methyl-2,1,3-benzoxadiazol-5-yl-1- or 3-N-oxide)
N-(4-methyl-6-bromo-2,1,3-benzoxadiazol-5-yl-1- or 3-N-oxide)
N-(4-methyl-7-bromo-2,1,3-benzoxadiazol-5-yl-1- or 3-N-oxide)
N-(6-methyl-7-bromo-2,1,3-benzoxadiazol-5-yl-1- or 3-N-oxide)
N-(4-bromo-6-ethyl-2,1,3-benzoxadiazol-5-yl-1- or 3-N-oxide)
N-(4-bromo-7-ethyl-2,1,3-benzoxadiazol-5-yl-1- or 3-N-oxide)
N-(6-bromo-7-ethyl-2,1,3-benzoxadiazol-5-yl-1- or 3-N-oxide)
N-(4-ethyl-6-bromo-2,1,3-benzoxadiazol-5-yl-1- or 3-N-oxide)
N-(4-ethyl-7-bromo-2,1,3-benzoxadiazol-5-yl-1- or 3-N-oxide)
N-(6-ethyl-7-bromo-2,1,3-benzoxadiazol-5-yl-1- or 3-N-oxide)
N-(4-bromo-6-trifluoromethyl-2,1,3-benzoxadiazol-5-yl-1- or 3-N-oxide)
N-(4-bromo-7-trifluoromethyl-2,1,3-benzoxadiazol-5-yl-1- or 3-N-oxide)
N-(6-bromo-7-trifluoromethyl-2,1,3-benzoxadiazol-5-yl-1- or 3-N-oxide)
N-(4-trifluoromethyl-6-bromo-2,1,3-benzoxadiazol-5-yl-1- or 3-N-oxide)
N-4-trifluoromethyl-7-bromo-2,1,3-benzoxadiazol-5-yl-1- or 3-N-oxide)
N-(6-trifluoromethyl-7-bromo-2,1,3-benzoxadiazol-5-yl-1- or 3-N-oxide)
N-(4-chloro-2,1,3-benzoxadiazol-5-yl-1- or 3-N-oxide)
N-(6-chloro-2,1,3-benzoxadiazol-5-yl-1- or 3-N-oxide)
N-(7-chloro-2,1,3-benzoxadiazol-5-yl-1- or 3-N-oxide)
N-(4-nitro-2,1,3-benzoxadiazol-5-yl-1- or 3-N-oxide)
N-(6-nitro-2,1,3-benzoxadiazol-5-yl-1- or 3-N-oxide)
N-(7-nitro-2,1,3-benzoxadiazol-5-yl-1- or 3-N-oxide)
N-(4-bromo-6-tert-butyl-2,1,3-benzoxadiazol-5-yl-1- or 3-N-oxide)
N-(4-bromo-7-tert-butyl-2,1,3-benzoxadiazol-5-yl-1- or 3-N-oxide)
N-(6-bromo-7-tert-butyl-2,1,3-benzoxadiazol-5-yl-1- or 3-N-oxide)
N-(4-tert-butyl-6-bromo-2,1,3-benzoxadiazol-5-yl-3- or 3-N-oxide)
N-(4-tert-butyl-7-bromo-2,1,3-benzoxadiazol-5-yl-1- or 3-N-oxide)
N-(6-tert-butyl-7-bromo-2,1,3-benzoxadiazol-5-yl-1- or 3-N-oxide)
N-(4-chloro-6-methyl-2,1,3-benzoxadiazol-5-yl-1- or 3-N-oxide)
N-(4-chloro-7-methyl-2,1,3-benzoxadiazol-5-yl-1- or 3-N-oxide)
N-(6-chloro-7-methyl-2,1,3-benzoxadiazol-5-yl-1- or 3-N-oxide)
N-(4-methyl-6-chloro-2,1,3-benzoxadiazol-5-yl-1- or 3-N-oxide)
N-(4-methyl-7-chloro-2,1,3-benzoxadiazol-5-yl-1- or 3-N-oxide)
N-(6-methyl-7-chloro-2,1,3-benzoxadiazol-5-yl-1- or 3-N-oxide)
N-(4-dimethylamino-2,1,3-benzoxadiazol-5-yl-1- or 3-N-oxide)
N-(6-dimethylamino-2,1,3-benzoxadiazol-5-yl-1- or 3-N-oxide)
N-(7-dimethylamino-2,1,3-benzoxadiazol-5-yl-1- or 3-N-oxide)
N-(4-cyano-2,1,3-benzoxadiazol-5-yl-1- or 3-N-oxide)
N-(6-cyano-2,1,3-benzoxadiazol-5-yl-1- or 3-N-oxide)
N-(7-cyano-2,1,3-benzoxadiazol-5-yl-1- or 3-N-oxide)
N-(4-methoxycarbonyl-2,1,3-benzoxadiazol-5-yl-1- or 3-N-oxide)
N-(6-methoxycarbonyl-2,1,3-benzoxadiazol-5-yl-1- or 3-N-oxide)
N-(7-methoxycarbonyl-2,1,3-benzoxadiazol-5-yl-1- or 3-N-oxide)
N-(4-ethoxycarbonyl-2,1,3-benzoxadiazol-5-yl-1- or 3-N-oxide)
N-(6-ethoxycarbonyl-2,1,3-benzoxadiazol-5-yl-1- or 3-N-oxide)
N-(7-ethoxycarbonyl-2,1,3-benzoxadiazol-5-yl-1- or 3-N-oxide)
N-(4-acetamino-2,1,3-benzoxadiazol-5-yl-1- or 3-N-oxide)
N-(6-acetamido-2,1,3-benzoxadiazol-5-yl-1- or 3-N-oxide)
N-(7-acetamido-2,1,3-benzoxadiazol-5-yl-1- or 3-N-oxide)
with triethyl phosphite, the 5-dimethylamino-mZ-1-naphthalenesulfonamides below are obtained in which mZ is N-(4-methyl-2,1,3-benzoxadiazol-5-yl)
N-(6-methyl-2,1,3-benzoxadiazol-5-yl)
N-(7-methyl-2,1,3-benzoxadiazol-5-yl)
N-(4,6-dimethyl-2,1,3-benzoxadiazol-5-yl)
N-(4,7-dimethyl-2,1,3-benzoxadiazol-5-yl)
N-(6,7-dimethyl-2,1,3-benzoxadiazol-5-yl)
N-(4-trifluoromethyl-2,1,3-benzoxadiazol-5-yl)
N-(6-trifluoromethyl-2,1,3-benzoxadiazol-5-yl)
N-(7-trifluoromethyl-2,1,3-benzoxadiazol-5-yl)
N-(4-bromo-2,1,3-benzoxadiazol-5-yl)
N-(6-bromo-2,1,3-benzoxadiazol-5-yl)
N-(7-bromo-2,1,3-benzoxadiazol-5-yl)
N-(4,6-dibromo-2,1,3-benzoxadiazol-5-yl)
N-(4,7-dibromo-2,1,3-benzoxadiazol-5-yl)
N-(6,7-dibromo-2,1,3-benzoxadiazol-5-yl)
N-(4-bromo-6-methyl-2,1,3-benzoxadiazol-5-yl)
N-(4-bromo-7-methyl-2,1,3-benzoxadiazol-5-yl)
N-(6-bromo-7-methyl-2,1,3-benzoxadiazol-5-yl)

N-(4-methyl-6-bromo-2,1,3-benzoxadiazol-5-yl)
N-(4-methyl-7-bromo-2,1,3-benzoxadiazol-5-yl)
N-(6-methyl-7-bromo-2,1,3-benzoxadiazol-5-yl)
N-(4-bromo-6-ethyl-2,1,3-benzoxadiazol-5-yl)
N-(4-bromo-7-ethyl-2,1,3-benzoxadiazol-5-yl)
N-(6-bromo-7-ethyl-2,1,3-benzoxadiazol-5-yl)
N-(4-ethyl-6-bromo-2,1,3-benzoxadiazol-5-yl)
N-(4-ethyl-7-bromo-2,1,3-benzoxadiazol-5-yl)
N-(6-ethyl-7-bromo-2,1,3-benzoxadiazol-5-yl)
N-(4-bromo-6-trifluoromethyl-2,1,3-benzoxadiazol-5-yl)
N-(4-bromo-7-trifluoromethyl-2,1,3-benzoxadiazol-5-yl)
N-(6-bromo-7-trifluoromethyl-2,1,3-benzoxadiazol-5-yl)
N-(4-trifluoromethyl-6-bromo-2,1,3-benzoxadiazol-5-yl)
N-(4-trifluoromethyl-7-bromo-2,1,3-benzoxadiazol-5-yl)
N-(6-trifluoromethyl-7-bromo-2,1,3-benzoxadiazol-5-yl)
N-(4-chloro-2,1,3-benzoxadiazol-5-yl)
N-(6-chloro-2,1,3-benzoxadiazol-5-yl)
N-(7-chloro-2,1,3-benzoxadiazol-5-yl)
N-(4-nitro-2,1,3-benzoxadiazol-5-yl)
N-(6-nitro-2,1,3-benzoxadiazol-5-yl)
N-(7-nitro-2,1,3-benzoxadiazol-5-yl)
N-(4-bromo-6-tert-butyl-2,1,3-benzoxadiazol-5-yl)
N-(4-bromo-7-tert-butyl-2,1,3-benzoxadiazol-5-yl)
N-(6-bromo-7-tert-butyl-2,1,3-benzoxadiazol-5-yl)
N-(4-tert-butyl-6-bromo-2,1,3-benzoxadiazol-5-yl)
N-(4-tert-butyl-7-bromo-2,1,3-benzoxadiazol-5-yl)
N-(6-tert-butyl-7-bromo-2,1,3-benzoxadiazol-5-yl
N-(4-chloro-6-methyl-2,1,3-benzoxadiazol-5-yl)
N-(4-chloro-7-methyl-2,1,3-benzoxadiazol-5-yl)
N-(6-chloro-7-methyl-2,1,3-benzoxadiazol-5-yl)
N-(4-methyl-6-chloro-2,1,3-benzoxadiazol-5-yl)
N-(4-methyl-7-chloro-2,1,3-benzoxadiazol-5-yl)
N-(6-methyl-7-chloro-2,1,3-benzoxadiazol-5-yl)
N-(4-dimethylamino-2,1,3-benzoxadiazol-5-yl)
N-(6-dimethylamino-2,1,3-benzoxadiazol-5-yl)
N-(7-dimethylamino-2,1,3-benzoxadiazol-5-yl)
N-(4-cyano-2,1,3-benzoxadiazol-5-yl)
N-(6-cyano-2,1,3-benzoxadiazol-5-yl)
N-(7-cyano-2,1,3-benzoxadiazol-5-yl)
N-(4-methoxycarbonyl-2,1,3-benzoxadiazol-5-yl)
N-(6-methoxycarbonyl-2,1,3-benzoxadiazol-5-yl)
N-(7-methoxycarbonyl-2,1,3-benzoxadiazol-5-yl)
N-(4-ethoxycarbonyl-2,1,3-benzoxadiazol-5-yl)
N-(6-ethoxycarbonyl-2,1,3-benzoxadiazol-5-yl)
N-(7-ethoxycarbonyl-2,1,3-benzoxadiazol-5-yl)
N-(4-acetamido-2,1,3-benzoxadiazol-5-yl)
N-(6-acetamido-2,1,3-benzoxadiazol-5-yl)
N-(7-acetamido-2,1,3-benzoxadiazol-5-yl).

Example 4

A solution of 1 g of 3-nitro-N-(2,1,3-benzothiadiazol-5-yl)-1-benzenesulfonamide in 25 ml of methanol is hydrogenated to completion on 1 g of Raney Nickel at normal pressure and 20°. The solution is filtered, evaporated and 3-amino-N-(2,1,3-benzothiadiazol-5-yl)-1-benzenesulfonamide is obtained.

Analogously, from 4-nitro-N-(2,1,3-benzothiadiazol-5-yl)-1-benzenesulfonamide
2-nitro-5-methyl-N-(2,1,3-benzothiadiazol-5-yl)-1-benzenesulfonamide
2-methyl-5-nitro-N-(2,1,3-benzothiadiazol-5-yl)-1-benzenesulfonamide
4-nitro-N-(2,1,3-benzoxadiazol-5-yl)-1-benzenesulfonamide
3-nitro-N-(2,1,3-benzoxadiazol-5-yl)-1-benzenesulfonamide
2-nitro-5-methyl-N-(2,1,3-benzoxadiazol-5-yl)-1-benzenesulfonamide
2-methyl-5-nitro-N-(2,1,3-benzoxadiazol-5-yl)-1-benzenesulfonamide the compounds below
4-amino-N-(2,1,3-benzothiadiazol-5-yl)-1-benzenesulfonamide
2-amino-5-methyl-N-(2,1,3-benzothiadiazol-5-yl)-1-benzenesulfonamide
2-amino-5-nitro-N-(2,1,3-benzothiadiazol-5-yl)-1-benzenesulfonamide
4-amino-N-(2,1,3-benzoxadiazol-5-yl)-1-benzenesulfonamide
3-amino-N-(2,1,3-benzoxadiazol-5-yl)-1-benzenesulfonamide
2-amino-5-methyl-N-(2,1,3-benzoxadiazol-5-yl)-1-benzenesulfonamide
2-methyl-5-amino-N-(2,1,3-benzoxadiazol-5-yl)-1-benzenesulfonamide are obtained.

Example 5

Analogously to Example 1, by reaction of 5-amino-2,1,3-benzoxadiazole (obtainable by reduction of 5-nitro-2,1,3-benzoxadiazole-1- or 3-N-oxide with triethyl phosphite) with 2-ethylbenzenesulfonyl chloride, 2-ethyl-N-(2,1,3-benzoxadiazol-5-yl)-1-benzenesulfonamide is obtained.

Analogously, from the 5-amino-mZ-2,1,3-benzoxadiazoles in which mZ is 4-methyl
6-methyl
7-methyl
4,6-dimethyl
4,7-dimethyl
6,7-dimethyl
4-trifluoromethyl
6-trifluoromethyl
7-trifluoromethyl
4-bromo
6-bromo
7-bromo
4,6-dibromo
4,7-dibromo
6,7-dibromo
4-bromo-6-methyl
4-bromo-7-methyl
6-bromo-7-methyl
4-methyl-6-bromo
4-methyl-7-bromo
6-methyl-7-bromo
4-bromo-6-ethyl
4-bromo-7-ethyl
6-bromo-7-ethyl
4-ethyl-6-bromo
4-ethyl-7-bromo
6-ethyl-7-bromo
4-bromo-6-trifluoromethyl
4-bromo-7-trifluoromethyl
6-bromo-7-trifluoromethyl
4-trifluoromethyl-6-bromo
4-trifluoromethyl-7-bromo
6-trifluoromethyl-7-bromo
4-chloro
6-chloro
7-chloro
4-nitro 6-nitro
7-nitro
4-bromo-6-tert-butyl
4-bromo-7-tert-butyl
6-bromo-7-tert-butyl
4-tert-butyl-6-bromo
4-tert-butyl-7-bromo
6-tert-butyl-7-bromo
4-chloro-6-methyl
4-chloro-7-methyl
6-chloro-7-methyl
4-methyl-6-chloro
4-methyl-7-chloro
6-methyl-7-chloro
4-dimethylamino
6-dimethylamino
7-dimethylamino
4-cyano
6-cyano
7-cyano
4-methoxycarbonyl
6-methoxycarbonyl
7-methoxycarbonyl
4-ethoxycarbonyl
6-ethoxycarbonyl
7-ethoxycarbonyl
4-acetamido
6-acetamido
7-acetamido by reaction with 2-ethylbenzenesulfonyl chloride the ethyl-mZ-1-benzenesulfonamides below are obtained in which mZ is N-(4-methyl-2,1,3-benzoxadiazol-5-yl)
N-(6-methyl-2,1,3-benzoxadiazol-5-yl)
N-(7-methyl-2,1,3-benzoxadiazol-5-yl)
N-(4,6-dimethyl-2,1,3-benzoxadiazol-5-yl)
N-(4,7-dimethyl-2,1,3-benzoxadiazol-5-yl)
N-(6,7-dimethyl-2,1,3-benzoxadiazol-5-yl)
N-(4-trifluoromethyl-2,1,3-benzoxadiazol-5-yl)
N-(6-trifluoromethyl-2,1,3-benzoxadiazol-5-yl)
N-(7-trifluoromethyl-2,1,3-benzoxadiazol-5-yl)
N-(4-bromo-2,1,3-benzoxadiazol-5-yl)
N-(6-bromo-2,1,3-benzoxadiazol-5-yl)
N-(7-bromo-2,1,3-benzoxadiazol-5-yl)
N-(4,6-dibromo-2,1,3-benzoxadiazol-5-yl)
N-(4,7-dibromo-2,1,3-benzoxadiazol-5-yl)
N-(6,7-dibromo-2,1,3-benzoxadiazol-5-yl)
N-(4-bromo-6-methyl-2,1,3-benzoxadiazol-5-yl)
N-(4-bromo-7-methyl-2,1,3-benzoxadiazol-5-yl)
N-(6-bromo-7-methyl-2,1,3-benzoxadiazol-5-yl)
N-(4-methyl-6-bromo-2,1,3-benzoxadiazol-5-yl)
N-(4-methyl-7-bromo-2,1,3-benzoxadiazol-5-yl)
N-(6-methyl-7-bromo-2,1,3-benzoxadiazol-5-yl)
N-(4-bromo-6-ethyl -2,1,3-benzoxadiazol-5-yl)
N-(4-bromo-7-ethyl -2,1,3-benzoxadiazol-5-yl)
N-(6-bromo-7-ethyl -2,1,3-benzoxadiazol-5-yl)
N-(4-ethyl-6-bromo-2,1,3-benzoxadiazol-5-yl)
N-(4-ethyl-7-bromo-2,1,3-benzoxadiazol-5-yl)
N-(6-ethyl-7-bromo-2,1,3-benzoxadiazol-5-yl)
N-(4-bromo-6-trifluoromethyl-2,1,3-benzoxadiazol-5-yl)
N-(4-bromo-7-trifluoromethyl-2,1,3-benzoxadiazol-5-yl)
N-(6-bromo-7-trifluoromethyl-2,1,3-benzoxadiazol-5-yl)
N-(4-trifluoromethyl-6-bromo-2,1,3-benzoxadiazol-5-yl)
N-(4-trifluoromethyl-7-bromo-2,1,3-benzoxadiazol-5-yl)
N-(6-trifluoromethyl-7-bromo-2,1,3-benzoxadiazol-5-yl)
N-(4-chloro-2,1,3-benzoxadiazol-5-yl)
N-(6-chloro-2,1,3-benzoxadiazol-5-yl)
N-(7-chloro-2,1,3-benzoxadiazol-5-yl)
N-(4-nitro-2,1,3-benzoxadiazol-5-yl)
N-(6-nitro-2,1,3-benzoxadiazol-5-yl)
N-(7-nitro-2,1,3-benzoxadiazol-5-yl)
N-(4-bromo-6-tert-butyl-2,1,3-benzoxadiazol-5-yl)
N-(4-bromo-7-tert-butyl-2,1,3-benzoxadiazol-5-yl)
N-(6-bromo-7-tert-butyl-2,1,3-benzoxadiazol-5-yl)
N-(4-tert-butyl-6-bromo-2,1,3-benzoxadiazol-5-yl)
N-(4-tert-butyl-7-bromo-2,1,3-benzoxadiazol-5-yl)
N-(6-tert-butyl-7-bromo-2,1,3-benzoxadiazol -5-yl)
N-(4-chloro-6-methyl-2,1,3-benzoxadiazol-5-yl)
N-(4-chloro-7-methyl-2,1,3-benzoxadiazol-5-yl)
N-(6-chloro-7-methyl-2,1,3-benzoxadiazol-5-yl)
N-(4-methyl-6-chloro-2,1,3-benzoxadiazol-5-yl)
N-(4-methyl-7-chloro-2,1,3-benzoxadiazol-5-yl)
N-(6-methyl-7-chloro-2,1,3-benzoxadiazol-5-yl)
N-(4-dimethylamino-2,1,3-benzoxadiazol-5-yl)
N-(6-dimethylamino-2,1,3-benzoxadiazol-5-yl)
N-(7-dimethylamino-2,1,3-benzoxadiazol-5-yl)
N-(4-cyano-2,1,3-benzoxadiazol-5-yl)
N-(6-cyano-2,1,3-benzoxadiazol-5-yl)
N-(7-cyano-2,1,3-benzoxadiazol-5-yl)
N-(4-methoxycarbonyl-2,1,3-benzoxadiazol-5-yl)
N-(6-methoxycarbonyl-2,1,3-benzoxadiazol-5-yl)
N-(7-methoxycarbonyl-2,1,3-benzoxadiazol-5-yl)
N-(4-ethoxycarbonyl-2,1,3-benzoxadiazol-5-yl)
N-(6-ethoxycarbonyl-2,1,3-benzoxadiazol-5-yl)
N-(7-ethoxycarbonyl-2,1,3-benzoxadiazol-5-yl)
N-(4-acetamido-2,1,3-benzoxadiazol-5-yl)
N-(6-acetamido-2,1,3-benzoxadiazol-5-yl)
N-(7-acetamido-2,1,3-benzoxadiazol-5-yl).

By corresponding reactions with 2-ethyl-5-bromobenzenesulfonyl chloride the 2-ethyl-5-bromo-mZ-1-benzenesulfonamides below are obtained in which mZ is N-(4-methyl-2,1,3-benzoxadiazol-5-yl)
N-(6-methyl-2,1,3-benzoxadiazol-5-yl)
N-(7-methyl-2,1,3-benzoxadiazol-5-yl)
N-(4,6-dimethyl-2,1,3-benzoxadiazol-5-yl)
N-(4,7-dimethyl-2,1,3-benzoxadiazol-5-yl)
N-(6,7-dimethyl-2,1,3-benzoxadiazol-5-yl)
N-(4-trifluoromethyl-2,1,3-benzoxadiazol-5-yl)
N-(6-trifluoromethyl-2,1,3-benzoxadiazol-5-yl)
N-(7-trifluoromethyl-2,1,3-benzoxadiazol-5-yl)
N-(4-bromo-2,1,3-benzoxadiazol-5-yl)
N-(6-bromo-2,1,3-benzoxadiazol-5-yl)
N-(7-bromo-2,1,3-benzoxadiazol-5-yl)
N-(4,6-dibromo-2,1,3-benzoxadiazol-5-yl)
N-(4,7-dibromo-2,1,3-benzoxadiazol-5-yl)
N-(6,7-dibromo-2,1,3-benzoxadiazol-5-yl)
N-(4-bromo-6-methyl-2,1,3-benzoxadiazol-5-yl)
N-(4-bromo-7-methyl-2,1,3-benzoxadiazol-5-yl)
N-(6-bromo-7-methyl-2,1,3-benzoxadiazol-5-yl)
N-(4-methyl-6-bromo-2,1,3-benzoxadiazol-5-yl)
N-(4-methyl-7-bromo-2,1,3-benzoxadiazol-5-yl)
N-(6-methyl-7-bromo-2,1,3-benzoxadiazol-5-yl)
N-(4-bromo-6-ethyl-2,1,3-benzoxadiazol-5-yl)
N-(4-bromo-7-ethyl-2,1,3-benzoxadiazol-5-yl)
N-(6-bromo-7-ethyl-2,1,3-benzoxadiazol-5-yl)
N-(4-ethyl-6-bromo-2,1,3-benzoxadiazol-5-yl)
N-(4-ethyl-7-bromo-2,1,3-benzoxadiazol-5-yl)
N-(6-ethyl-7-bromo-2,1,3-benzoxadiazol-5-yl)
N-(4-bromo-6-trifluoromethyl-2,1,3-benzoxadiazol-5-yl)
N-(4-bromo-7-trifluoromethyl-2,1,3-benzoxadiazol-5-yl)
N-(6-bromo-7-trifluoromethyl-2,1,3-benzoxadiazol-5-yl)

N-(4-trifluoromethyl-6-bromo-2,1,3-benzoxadiazol-5-yl)
N-(4-trifluoromethyl-7-bromo-2,1,3-benzoxadiazol-5-yl)
N-(6-trifluoromethyl-7-bromo-2,1,3-benzoxadiazol-5-yl)
N-(4-chloro-2,1,3-benzoxadiazol-5-yl)
N-(6-chloro-2,1,3-benzoxadiazol-5-yl)
N-(7-chloro-2,1,3-benzoxadiazol-5-yl)
N-(4-nitro-2,1,3-benzoxadiazol-5-yl)
N-(6-nitro-2,1,3-benzoxadiazol-5-yl)
N-(7-nitro-2,1,3-benzoxadiazol-5-yl)
N-(4-bromo-6-tert-butyl-2,1,3-benzoxadiazol-5-yl)
N-(4-bromo-7-tert-butyl-2,1,3-benzoxadiazol-5-yl)
N-(6-bromo-7-tert-butyl-2,1,3-benzoxadiazol-5-yl)
N-(4-tert-butyl-6-bromo-2,1,3-benzoxadiazol-5-yl)
N-(4-tert-butyl-7-bromo-2,1,3-benzoxadiazol-5-yl)
N-(6-tert-butyl-7-bromo-2,1,3-benzoxadiazol -5-yl)
N-(4-chloro-6-methyl-2,1,3-benzoxadiazol-5-yl)
N-(4-chloro-7-methyl-2,1,3-benzoxadiazol-5-yl)
N-(6-chloro-7-methyl-2,1,3-benzoxadiazol-5-yl)
N-(4-methyl-6-chloro-2,1,3-benzoxadiazol-5-yl)
N-(4-methyl-7-chloro-2,1,3-benzoxadiazol-5-yl)
N-(6-methyl-7-chloro-2,1,3-benzoxadiazol-5-yl)
N-(4-dimethylamino-2,1,3-benzoxadiazol-5-yl)
N-(6-dimethylamino-2,1,3-benzoxadiazol-5-yl)
N-(7-dimethylamino-2,1,3-benzoxadiazol-5-yl)
N-(4-cyano-2,1,3-benzoxadiazol-5-yl)
N-(6-cyano-2,1,3-benzoxadiazol-5-yl)
N-(7-cyano-2,1,3-benzoxadiazol-5-yl)
N-(4-methoxycarbonyl-2,1,3-benzoxadiazol-5-yl)
N-(6-methoxycarbonyl-2,1,3-benzoxadiazol-5-yl)
N-(7-methoxycarbonyl-2,1,3-benzoxadiazol-5-yl)
N-(4-ethoxycarbonyl-2,1,3-benzoxadiazol-5-yl)
N-(6-ethoxycarbonyl-2,1,3-benzoxadiazol-5-yl)
N-(7-ethoxycarbonyl-2,1,3-benzoxadiazol-5-yl)
N-(4-acetamido-2,1,3-benzoxadiazol-5-yl)
N-(6-acetamido-2,1,3-benzoxadiazol-5-yl)
N-(7-acetamido-2,1,3-benzoxadiazol-5-yl),
and by analogous reaction with 2-propyl-5-bromobenzenesulfonyl chloride the 2-propyl-5-bromo-mZ-1-benzenesulfonamides below are obtained in which mZ is N-(4-methyl-2,1,3-benzoxadiazol-5-yl)
N-(6-methyl-2,1,3-benzoxadiazol-5-yl)
N-(7-methyl-2,1,3-benzoxadiazol-5-yl)
N-(4,6-dimethyl-2,1,3-benzoxadiazol-5-yl)
N-(4,7-dimethyl-2,1,3-benzoxadiazol-5-yl)
N-(6,7-dimethyl-2,1,3-benzoxadiazol-5-yl)
N-(4-trifluoromethyl-2,1,3-benzoxadiazol-5-yl)
N-(6-trifluoromethyl-2,1,3-benzoxadiazol-5-yl)
N-(7-trifluoromethyl-2,1,3-benzoxadiazol-5-yl)
N-(4-bromo-2,1,3-benzoxadiazol-5-yl)
N-(6-bromo-2,1,3-benzoxadiazol-5-yl)
N-(7-bromo-2,1,3-benzoxadiazol-5-yl)
N-(4,6-dibromo-2,1,3-benzoxadiazol-5-yl)
N-(4,7-dibromo-2,1,3-benzoxadiazol-5-yl)
N-(6,7-dibromo-2,1,3-benzoxadiazol-5-yl)
N-(4-bromo-6-methyl-2,1,3-benzoxadiazol-5-yl)
N-(4-bromo-7-methyl-2,1,3-benzoxadiazol-5-yl)
N-(6-bromo-7-methyl-2,1,3-benzoxadiazol-5-yl)
N-(4-methyl-6-bromo-2,1,3-benzoxadiazol-5-yl)
N-(4-methyl-7-bromo-2,1,3-benzoxadiazol-5-yl)
N-(6-methyl-7-bromo-2,1,3-benzoxadiazol-5-yl)
N-(4-bromo-6-ethyl-2,1,3-benzoxadiazol-5-yl)
N-(4-bromo-7-ethyl-2,1,3-benzoxadiazol-5-yl)
N-(6-bromo-7-ethyl-2,1,3-benzoxadiazol-5-yl)
N-(4-ethyl-6-bromo-2,1,3-benzoxadiazol-5-yl)
N-(4-ethyl-7-bromo-2,1,3-benzoxadiazol-5-yl)
N-(6-ethyl-7-bromo-2,1,3-benzoxadiazol-5-yl)
N-(4-bromo-6-trifluoromethyl-2,1,3-benzoxadiazol-5-yl)
N-(4-bromo-7-trifluoromethyl-2,1,3-benzoxadiazol-5-yl)
N-(6-bromo-7-trifluoromethyl-2,1,3-benzoxadiazol-5-yl)
N-(4-trifluoromethyl-6-bromo-2,1,3-benzoxadiazol-5-yl)
N-(4-trifluoromethyl-7-bromo-2,1,3-benzoxadiazol-5-yl)
N-(6-trifluoromethyl-7-bromo-2,1,3-benzoxadiazol-5-yl)
N-(4-chloro-2,1,3-benzoxadiazol-5-yl)
N-(6-chloro-2,1,3-benzoxadiazol-5-yl)
N-(7-chloro-2,1,3-benzoxadiazol-5-yl)
N-(4-nitro-2,1,3-benzoxadiazol-5-yl)
N-(6-nitro-2,1,3-benzoxadiazol-5-yl)
N-(7-nitro-2,1,3-benzoxadiazol-5-yl)
N-(4-bromo-6-tert-butyl-2,1,3-benzoxadiazol-5-yl)
N-(4-bromo-7-tert-butyl-2,1,3-benzoxadiazol-5-yl)
N-(6-bromo-7-tert-butyl-2,1,3-benzoxadiazol-5-yl)
N-(4-tert-butyl-6-bromo-2,1,3-benzoxadiazol-5-yl)
N-(4-tert-butyl-7-bromo-2,1,3-benzoxadiazol-5-yl)
N-(6-tert-butyl-7-bromo-2,1,3-benzoxadiazol-5-yl)
N-(4-chloro-6-methyl-2,1,3-benzoxadiazol-5-yl)
N-(4-chloro-7-methyl-2,1,3-benzoxadiazol-5-yl)
N-(6-chloro-7-methyl-2,1,3-benzoxadiazol-5-yl)
N-(4-methyl-6-chloro-2,1,3-benzoxadiazol-5-yl)
N-(4-methyl-7-chloro-2,1,3-benzoxadiazol-5-yl)
N-(6-methyl-7-chloro-2,1,3-benzoxadiazol-5-yl)
N-(4-dimethylamino-2,1,3-benzoxadiazol-5-yl)
N-(6-dimethylamino-2,1,3-benzoxadiazol-5-yl)
N-(7-dimethylamino-2,1,3-benzoxadiazol-5-yl)
N-(4-cyano-2,1,3-benzoxadiazol-5-yl)
N-(6-cyano-2,1,3-benzoxadiazol-5-yl)
N-(7-cyano-2,1,3-benzoxadiazol-5-yl)
N-(4-methoxycarbonyl-2,1,3-benzoxadiazol-5-yl
N-(6-methoxycarbonyl-2,1,3-benzoxadiazol-5-yl
N-(7-methoxycarbonyl-2,1,3-benzoxadiazol-5-yl
N-(4-ethoxycarbonyl-2,1,3-benzoxadiazol-5-yl)
N-(6-ethoxycarbonyl-2,1,3-benzoxadiazol-5-yl)
N-(7-ethoxycarbonyl-2,1,3-benzoxadiazol-5-yl)
N-(4-acetamido-2,1,3-benzoxadiazol-5-yl)
N-(6-acetamido-2,1,3-benzoxadiazol-5-yl)
N-(7-acetamido-2,1,3-benzoxadiazol-5-yl).

Analogously, from the 5-amino-mZ-2,1,3-benzothiadiazoles in which mZ is 4-methyl
6-methyl
7-methyl
4,6-dimethyl
4,7-dimethyl
6,7-dimethyl
4-trifluoromethyl
6-trifluoromethyl
7-trifluoromethyl
4-bromo
6-bromo
7-bromo
4,6-dibromo
4,7-dibromo
6,7-dibromo
4-bromo-6-methyl
4-bromo-7-methyl
6-bromo-7-methyl
4-methyl-6-bromo
4-methyl-7-bromo
6-methyl-7-bromo
4-bromo-6-ethyl
4-bromo-7-ethyl
6-bromo-7-ethyl 4-ethyl-6-bromo
4-ethyl-7-bromo
6-ethyl-7-bromo
4-bromo-6-trifluoromethyl
4-bromo-7-trifluoromethyl
6-bromo-7-trifluoromethyl
4-trifluoromethyl-6-bromo
4-trifluoromethyl-7-bromo
6-trifluoromethyl-7-bromo
4-chloro
6-chloro
7-chloro
4-nitro
6-nitro
7-nitro
4-bromo-6-tert-butyl
4-bromo-7-tert-butyl
6-bromo-7-tert-butyl
4-tert-butyl-6-bromo
4-tert-butyl-7-bromo
6-tert-butyl-7-bromo
4-chloro-6-methyl
4-chloro-7-methyl
6-chloro-7-methyl
4-methyl-6-chloro
4-methyl-7-chloro
6-methyl-7-chloro
4-dimethylamino
6-dimethylamino
7-dimethylamino
4-cyano
6-cyano
7-cyano
4-methoxycarbonyl
6-methoxycarbonyl
7-methoxycarbonyl
4-ethoxycarbonyl
6-ethoxycarbonyl
7-ethoxycarbonyl
4-acetamido
6-acetamido
7-acetamido by reaction with 2-ethylbenzenesulfonyl chloride 2-ethyl-mZ-1-benzenesulfonamides below are obtained in which mZ is N-(4-methyl-2,1,3-benzothiadiazol-5-yl)
N-(6-methyl-2,1,3-benzothiadiazol-5-yl)
N-(7-methyl-2,1,3-benzothiadiazol-5-yl)
N-(4,6-dimethyl-2,1,3-benzothiadiazol-5-yl)
N-(4,7-dimethyl-2,1,3-benzothiadiazol-5-yl)
N-(6,7-dimethyl-2,1,3-benzothiadiazol-5-yl)
N-(4-trifluoromethyl-2,1,3-benzothiadiazol-5-yl)
N-(6-trifluoromethyl-2,1,3-benzothiadiazol-5-yl)
N-(7-trifluoromethyl-2,1,3-benzothiadiazol-5-yl)
N-(4-bromo-2,1,3-benzothiadiazol-5-yl)
N-(6-bromo-2,1,3-benzothiadiazol-5-yl)
N-(7-bromo-2,1,3-benzothiadiazol-5-yl)
N-(4,6-dibromo-2,1,3-benzothiadiazol-5-yl)
N-(4,7-dibromo-2,1,3-benzothiadiazol-5-yl)
N-(6,7-dibromo-2,1,3-benzothiadiazol-5-yl)
N-(4-bromo-6-methyl-2,1,3-benzothiadiazol-5-yl)
N-(4-bromo-7-methyl-2,1,3-benzothiadiazol-5-yl)
N-(6-bromo-7-methyl-2,1,3-benzothiadiazol-5-yl)
N-(4-methyl-6-bromo-2,1,3-benzothiadiazol-5-yl)
N-(4-methyl-7-bromo-2,1,3-benzothiadiazol-5-yl)
N-(6-methyl-7-bromo-2,1,3-benzothiadiazol-5-yl)

N-(4-bromo-6-ethyl-2,1,3-benzothiadiazol-5-yl)
N-(4-bromo-7-ethyl-2,1,3-benzothiadiazol-5-yl)
N-(6-bromo-7-ethyl-2,1,3-benzothiadiazol-5-yl)
N-(4-ethyl-6-bromo-2,1,3-benzothiadiazol-5-yl)
N-(4-ethyl-7-bromo-2,1,3-benzothiadiazol-5-yl)
N-(6-ethyl-7-bromo-2,1,3-benzothiadiazol-5-yl)
N-(4-bromo-6-trifluoromethyl-2,1,3-benzothiadiazol-5-yl)
N-(4-bromo-7-trifluoromethyl-2,1,3-benzothiadiazol-5-yl)
N-(6-bromo-7-trifluoromethyl-2,1,3-benzothiadiazol-5-yl)
N-(4-trifluoromethyl-6-bromo-2,1,3-benzothiadiazol-5-yl)
N-(4-trifluoromethyl-7-bromo-2,1,3-benzothiadiazol-5-yl)
N-(6-trifluoromethyl-7-bromo-2,1,3-benzothiadiazol-5-yl)
N-(4-chloro-2,1,3-benzothiadiazol-5-yl)
N-(6-chloro-2,1,3-benzothiadiazol-5-yl)
N-(7-chloro-2,1,3-benzothiadiazol-5-yl)
N-(4-nitro-2,1,3-benzothiadiazol-5-yl)
N-(6-nitro-2,1,3-benzothiadiazol-5-yl)
N-(7-nitro-2,1,3-benzothiadiazol-5-yl)
N-(4-bromo-6-tert-butyl-2,1,3-benzothiadiazol-5-yl)
N-(4-bromo-7-tert-butyl-2,1,3-benzothiadiazol-5-yl)
N-(6-bromo-7-tert-butyl-2,1,3-benzothiadiazol-5-yl)
N-(4-tert-butyl-6-bromo-2,1,3-benzothiadiazol-5-yl)
N-(4-tert-butyl-7-bromo-2,1,3-benzothiadiazol-5-yl)
N-(6-tert-butyl-7-bromo-2,1,3-benzothiadiazol-5-yl)
N-(4-chloro-6-methyl-2,1,3-benzothiadiazol-5-yl)
N-(4-chloro-7-methyl-2,1,3-benzothiadiazol-5-yl)
N-(6-chloro-7-methyl-2,1,3-benzothiadiazol-5-yl)
N-(4-methyl-6-chloro-2,1,3-benzothiadiazol-5-yl)
N-(4-methyl-7-chloro-2,1,3-benzothiadiazol-5-yl)
N-(6-methyl-7-chloro-2,1,3-benzothiadiazol-5-yl)
N-(4-dimethylamino-2,1,3-benzothiadiazol-5-yl)
N-(6-dimethylamino-2,1,3-benzothiadiazol-5-yl)
N-(7-dimethylamino-2,1,3-benzothiadiazol-5-yl)
N-(4-cyano-2,1,3-benzothiadiazol-5-yl)
N-(6-cyano-2,1,3-benzothiadiazol-5-yl)
N-(7-cyano-2,1,3-benzothiadiazol-5-yl)
N-(4-methoxycarbonyl-2,1,3-benzothiadiazol-5-yl)
N-(6-methoxycarbonyl-2,1,3-benzothiadiazol-5-yl)
N-(7-methoxycarbonyl-2,1,3-benzothiadiazol-5-yl)
N-(4-ethoxycarbonyl-2,1,3-benzothiadiazol-5-yl)
N-(6-ethoxycarbonyl-2,1,3-benzothiadiazol-5-yl)
N-(7-ethoxycarbonyl-2,1,3-benzothiadiazol-5-yl)
N-(4-acetamido-2,1,3-benzothiadiazol-5-yl)
N-(6-acetamido-2,1,3-benzothiadiazol-5-yl)
N-(7-acetamido-2,1,3-benzothiadiazol-5-yl), and by analogous reaction with 2-ethyl-5-bromobenzenesulfonyl chloride the 2-ethyl-5-bromo-mZ-1-benzenesulfonamides below are obtained in which mZ is N-(4-methyl-2,1,3-benzothiadiazol-5-yl)
N-(6-methyl-2,1,3-benzothiadiazol-5-yl)
N-(7-methyl-2,1,3-benzothiadiazol-5-yl)
N-(4,6-dimethyl-2,1,3-benzothiadiazol-5-yl)
N-(4,7-dimethyl-2,1,3-benzothiadiazol-5-yl)
N-(6,7-dimethyl-2,1,3-benzothiadiazol-5-yl)
N-(4-trifluoromethyl-2,1,3-benzothiadiazol-5-yl)
N-(6-trifluoromethyl-2,1,3-benzothiadiazol-5-yl)
N-(7-trifluoromethyl-2,1,3-benzothiadiazol-5-yl)
N-(4-bromo-2,1,3-benzothiadiazol-5-yl)
N-(6-bromo-2,1,3-benzothiadiazol-5-yl)
N-(7-bromo-2,1,3-benzothiadiazol-5-yl)
N-(4,6-dibromo-2,1,3-benzothiadiazol-5-yl)
N-(4,7-dibromo-2,1,3-benzothiadiazol-5-yl)
N-(6,7-dibromo-2,1,3-benzothiadiazol-5-yl)
N-(4-bromo-6-methyl-2,1,3-benzothiadiazol-5-yl)
N-(4-bromo-7-methyl-2,1,3-benzothiadiazol-5-yl)
N-(6-bromo-7-methyl-2,1,3-benzothiadiazol-5-yl)

N-(4-methyl-6-bromo-2,1,3-benzothiadiazol-5-yl)
N-(4-methyl-7-bromo-2,1,3-benzothiadiazol-5-yl)
N-(6-methyl-7-bromo-2,1,3-benzothiadiazol-5-yl)
N-(4-bromo-6-ethyl-2,1,3-benzothiadiazol-5-yl)
N-(4-bromo-7-ethyl-2,1,3-benzothiadiazol-5-yl)
N-(6-bromo-7-ethyl-2,1,3-benzothiadiazol-5-yl)
N-(4-ethyl-6-bromo-2,1,3-benzothiadiazol-5-yl)
N-(4-ethyl-7-bromo-2,1,3-benzothiadiazol-5-yl)
N-(6-ethyl-7-bromo-2,1,3-benzothiadiazol-5-yl)
N-(4-bromo-6-trifluoromethyl-2,1,3-benzothiadiazol-5-yl)
N-(4-bromo-7-trifluoromethyl-2,1,3-benzothiadiazol-5-yl)
N-(6-bromo-7-trifluoromethyl-2,1,3-benzothiadiazol-5-yl)
N-(4-trifluoromethyl-6-bromo-2,1,3-benzothiadiazol-5-yl)
N-(4-trifluoromethyl-7-bromo-2,1,3-benzothiadiazol-5-yl)
N-(6-trifluoromethyl-7-bromo-2,1,3-benzothiadiazol-5-yl)
N-(4-chloro-2,1,3-benzothiadiazol-5-yl)
N-(6-chloro-2,1,3-benzothiadiazol-5-yl)
N-(7-chloro-2,1,3-benzothiadiazol-5-yl)
N-(4-nitro-2,1,3-benzothiadiazol-5-yl)
N-(6-nitro-2,1,3-benzothiadiazol-5-yl)
N-(7-nitro-2,1,3-benzothiadiazol-5-yl)
N-(4-bromo-6-tert-butyl-2,1,3-benzothiadiazol-5-yl)
N-(4-bromo-7-tert-butyl-2,1,3-benzothiadiazol-5-yl)
N-(6-bromo-7-tert-butyl-2,1,3-benzothiadiazol-5-yl)
N-(4-tert-butyl-6-bromo-2,1,3-benzothiadiazol-5-yl)
N-(4-tert-butyl-7-bromo-2,1,3-benzothiadiazol-5-yl)
N-(6-tert-butyl-7-bromo-2,1,3-benzothiadiazol-5-yl)
N-(4-chloro-6-methyl-2,1,3-benzothiadiazol-5-yl)
N-(4-chloro-7-methyl-2,1,3-benzothiadiazol-5-yl)
N-(6-chloro-7-methyl-2,1,3-benzothiadiazol-5-yl)
N-(4-methyl-6-chloro-2,1,3-benzothiadiazol-5-yl)
N-(4-methyl-7-chloro-2,1,3-benzothiadiazol-5-yl)
N-(6-methyl-7-chloro-2,1,3-benzothiadiazol-5-yl)
N-(4-dimethylamino-2,1,3-benzothiadiazol-5-yl)
N-(6-dimethylamino-2,1,3-benzothiadiazol-5-yl),
N-(7-dimethylamino-2,1,3-benzothiadiazol-5-yl)
N-(4-cyano-2,1,3-benzothiadiazol-5-yl)
N-(6-cyano-2,1,3-benzothiadiazol-5-yl)
N-(7-cyano-2,1,3-benzothiadiazol-5-yl)
N-(4-methoxycarbonyl-2,1,3-benzothiadiazol-5-yl)
N-(6-methoxycarbonyl-2,1,3-benzothiadiazol-5-yl)
N-(7-methoxycarbonyl-2,1,3-benzothiadiazol-5-yl)
N-(4-ethoxycarbonyl-2,1,3-benzothiadiazol-5-yl)
N-(6-ethoxycarbonyl-2,1,3-benzothiadiazol-5-yl)
N-(7-ethoxycarbonyl-2,1,3-benzothiadiazol-5-yl)
N-(4-acetamido-2,1,3-benzothiadiazol-5-yl)
N-(6-acetamido-2,1,3-benzothiadiazol-5-yl)
N-(7-acetamido-2,1,3-benzothiadiazol-5-yl),
and by analogous reaction with 2-propyl-5-bromobenzenesulfonyl chloride the 2-propyl-5-bromo-mZ-1-benzenesulfonamides below are obtained in which mZ is N-(4-methyl-2,1,3-benzothiadiazol-5-yl)
N-(6-methyl-2,1,3-benzothiadiazol-5-yl)
N-(7-methyl-2,1,3-benzothiadiazol-5-yl)
N-(4,6-dimethyl -2,1,3-benzothiadiazol-5-yl)
N-(4,7-dimethyl -2,1,3-benzothiadiazol-5-yl)
N-(6,7-dimethyl -2,1,3-benzothiadiazol-5-yl)
N-(4-trifluoromethyl-2,1,3-benzothiadiazol-5-yl)
N-(6-trifluoromethyl-2,1,3-benzothiadiazol-5-yl)
N-(7-trifluoromethyl-2,1,3-benzothiadiazol-5-yl)
N-(4-bromo-2,1,3-benzothiadiazol-5-yl)
N-(6-bromo-2,1,3-benzothiadiazol-5-yl)
N-(7-bromo-2,1,3-benzothiadiazol-5-yl)
N-(4,6-dibromo-2,1,3-benzothiadiazol-5-yl)
N-(4,7-dibromo-2,1,3-benzothiadiazol-5-yl)
N-(6,7-dibromo-2,1,3-benzothiadiazol-5-yl)
N-(4-bromo-6-methyl-2,1,3-benzothiadiazol-5-yl)
N-(4-bromo-7-methyl-2,1,3-benzothiadiazol-5-yl)
N-(6-bromo-7-methyl-2,1,3-benzothiadiazol-5-yl)
N-(4-methyl-6-bromo-2,1,3-benzothiadiazol-5-yl)
N-(4-methyl-7-bromo-2,1,3-benzothiadiazol-5-yl)
N-(6-methyl-7-bromo-2,1,3-benzothiadiazol-5-yl)
N-(4-bromo-6-ethyl-2,1,3-benzothiadiazol-5-yl)
N-(4-bromo-7-ethyl-2,1,3-benzothiadiazol-5-yl)
N-(6-bromo-7-ethyl-2,1,3-benzothiadiazol-5-yl)
N-(4-ethyl-6-bromo-2,1,3-benzothiadiazol-5-yl)
N-(4-ethyl-7-bromo-2,1,3-benzothiadiazol-5-yl)
N-(6-ethyl-7-bromo-2,1,3-benzothiadiazol-5-yl)
N-(4-bromo-6-trifluoromethyl-2,1,3-benzothiadiazol-5-yl)
N-(4-bromo-7-trifluoromethyl-2,1,3-benzothiadiazol-5-yl)
N-(6-bromo-7-trifluoromethyl-2,1,3-benzothiadiazol-5-yl)
N-(4-trifluoromethyl-6-bromo-2,1,3-benzothiadiazol-5-yl)
N-(4-trifluoromethyl-7-bromo-2,1,3-benzothiadiazol-5-yl)
N-(6-trifluoromethyl-7-bromo-2,1,3-benzothiadiazol-5-yl)
N-(4-chloro-2,1,3-benzothiadiazol-5-yl)
N-(6-chloro-2,1,3-benzothiadiazol-5-yl)
N-(7-chloro-2,1,3-benzothiadiazol-5-yl)
N-(4-nitro-2,1,3-benzothiadiazol-5-yl)
N-(6-nitro-2,1,3-benzothiadiazol-5-yl)
N-(7-nitro-2,1,3-benzothiadiazol-5-yl),
N-(4-bromo-6-tert-butyl-2,1,3-benzothiadiazol-5-yl)
N-(4-bromo-7-tert-butyl-2,1,3-benzothiadiazol-5-yl)
N-(6-bromo-7-tert-butyl-2,1,3-benzothiadiazol-5-yl)
N-(4-tert-butyl-6-bromo-2,1,3-benzothiadiazol-5-yl)
N-(4-tert-butyl-7-bromo-2,1,3-benzothiadiazol-5-yl)
N-(6-tert-butyl-7-bromo-2,1,3-benzothiadiazol-5-yl)
N-(4-chloro-6-methyl-2,1,3-benzothiadiazol-5-yl)
N-(4-chloro-7-methyl-2,1,3-benzothiadiazol-5-yl)
N-(6-chloro-7-methyl-2,1,3-benzothiadiazol-5-yl)
N-(4-methyl-6-chloro-2,1,3-benzothiadiazol-5-yl)
N-(4-methyl-7-chloro-2,1,3-benzothiadiazol-5-yl)
N-(6-methyl-7-chloro-2,1,3-benzothiadiazol-5-yl)
N-(4-dimethylamino-2,1,3-benzothiadiazol-5-yl)
N-(6-dimethylamino-2,1,3-benzothiadiazol-5-yl)
N-(7-dimethylamino-2,1,3-benzothiadiazol-5-yl)
N-(4-cyano-2,1,3-benzothiadiazol-5-yl)
N-(6-cyano-2,1,3-benzothiadiazol-5-yl)
N-(7-cyano-2,1,3-benzothiadiazol-5-yl)
N-(4-methoxycarbonyl-2,1,3-benzothiadiazol-5-yl)
N-(6-methoxycarbonyl-2,1,3-benzothiadiazol-5-yl)
N-(7-methoxycarbonyl-2,1,3-benzothiadiazol-5-yl)
N-(4-ethoxycarbonyl-2,1,3-benzothiadiazol-5-yl)
N-(6-ethoxycarbonyl-2,1,3-benzothiadiazol-5-yl)
N-(7-ethoxycarbonyl-2,1,3-benzothiadiazol-5-yl)
N-(4-acetamido-2,1,3-benzothiadiazol-5-yl)
N-(6-acetamido-2,1,3-benzothiadiazol-5-yl)
N-(7-acetamido-2,1,3-benzothiadiazol-5-yl).

Example 6

Analogously to Example 1, by reaction of 6-amino-1,2,5-oxadiazolo[3,4-b]pyridine with "A" 5-dimethylamino-N-(1,2,5-oxadiazolo[3,4-b]pyridin-6-yl)-1-naphthalenesulfonamide is obtained.

Analogously, from the following mZ-6-amino-1,2,5-oxadiazolo[3,4-b]pyridines in which mZ is 5-methyl
7-methyl
5,7-dimethyl
5-trifluoromethyl
7-trifluoromethyl
5-bromo
7-bromo 5,7-dibromo
5-bromo-7-methyl
5-methyl-7-bromo
5-bromo-7-ethyl
5-ethyl-7-bromo
5-bromo-7-trifluoromethyl
5-trifluoromethyl-7-bromo
5-chloro
7-chloro
5-nitro
7-nitro
5-bromo-7-tert-butyl
5-tert-butyl-7-bromo
5-chloro-7-methyl
5-methyl-7-chloro
5-dimethylamino
7-dimethylamino
5-cyano
7-cyano
5-methoxycarbonyl
7-methoxycarbonyl
5-ethoxycarbonyl
7-ethoxycarbonyl
5-acetamino
7-acetamino by reaction with "A", the 5-dimethylamino-N-(mZ-1,2,5-oxadiazolo[3,4-b]pyridin-6-yl)-1-naphthalene-sulfonamides below are obtained in which mZ is 5-methyl
7-methyl
5,7-dimethyl
5-trifluoromethyl
7-trifluoromethyl
5-bromo
7-bromo
5,7-dibromo
5-bromo-7-methyl
5-methyl-7-bromo
5-bromo-7-ethyl
5-ethyl-7-bromo
5-bromo-7-trifluoromethyl
5-trifluoromethyl-7-bromo
5-chloro
7-chloro
5-nitro
7-nitro
5-bromo-7-tert-butyl
5-tert-butyl-7-bromo
5-chloro-7-methyl
5-methyl-7-chloro
5-dimethylamino
7-dimethylamino
5-cyano
7-cyano
5-methoxycarbonyl
7-methoxycarbonyl
5-ethoxycarbonyl
7-ethoxycarbonyl
5-acetamido
7-acetamido.

Analogously, by reaction of 6-amino-1,2,5-thiadiazolo[3,4-b]pyridine with "A", 5-dimethylamino-N-(1,2,5-thiadiazolo[3,4-b]pyridin-6-yl)-1-naphthalenesulfonamide is obtained.

Analogously, from the following mZ-6-amino-1,2,5-thiadiazolo[3,4-b]pyridines in which mZ is 5-methyl
7-methyl
5,7-dimethyl
5-trifluoromethyl
7-trifluoromethyl
5-bromo
7-bromo
5,7-dibromo
5-bromo-7-methyl
5-methyl-7-bromo
5-bromo-7-ethyl
5-ethyl-7-bromo
5-bromo-7-trifluoromethyl
5-trifluoromethyl-7-bromo
5-chloro
7-chloro
5-nitro
7-nitro
5-bromo-7-tert-butyl
5-tert-butyl-7-bromo
5-chloro-7-methyl
5-methyl-7-chloro
5-dimethylamino
7-dimethylamino
5-cyano
7-cyano
5-methoxycarbonyl
7-methoxycarbonyl
5-ethoxycarbonyl
7-ethoxycarbonyl
5-acetamido
7-acetamido by reaction with "A", the 5-dimethylamino-N-(mZ-1,2,5-thiadiazolo[3,4-b]pyridin-6-yl)-1-naphthalene-sulfonamides below are obtained in which mZ is 5-methyl, m.p. 192°
7-methyl
5,7-dimethyl
5-trifluoromethyl
7-trifluoromethyl
5-bromo
7-bromo
5,7-dibromo
5-bromo-7-methyl
5-methyl-7-bromo
5-bromo-7-ethyl
5-ethyl-7-bromo
5-bromo-7-trifluoromethyl
5-trifluoromethyl-7-bromo
5-chloro
7-chloro
5-nitro
7-nitro
5-bromo-7-tert-butyl
5-tert-butyl-7-bromo
5-chloro-7-methyl
5-methyl-7-chloro
5-dimethylamino
7-dimethylamino
5-cyano
7-cyano
5-methoxycarbonyl
7-methoxycarbonyl
5-ethoxycarbonyl
7-ethoxycarbonyl 5-acetamido
7-acetamido.

Analogously, by reaction of 5-amino-1,2,5-thiadiazolo[3,4-b]pyridine with "A" 5-dimethylamino-N-(1,2,5-thiadiazolo[3,4-b]pyridin-5-yl)-1-naphthalenesulfonamide is obtained.

Analogously, by reaction of 7-amino-1,2,5-oxadiazolo[3,4-b]pyridine with "A" 5-dimethylamino-N-(1,2,5-oxadiazolo[3,4-b]pyridin-7-yl)-1-naphthalenesulfonamide is obtained.

Analogously, from the following mZ-7-amino-1,2,5-oxadiazolo[3,4-b]pyridines in which mZ is 5-methyl
6-methyl
5,6-dimethyl
5-trifluoromethyl
6-trifluoromethyl
5-bromo
6-bromo
5,6-dibromo
5-bromo-6-methyl
5-methyl-6-bromo
5-bromo-6-ethyl
5-ethyl-6-bromo
5-bromo-6-trifluoromethyl
5-trifluoromethyl-6-bromo
5-chloro
6-chloro
5-nitro
6-nitro
5-bromo-6-tert-butyl
5-tert-butyl-6-bromo
5-chloro-6-methyl
5-methyl-6-chloro
5-dimethylamino
6-dimethylamino
5-cyano
6-cyano
5-methoxycarbonyl
6-methoxycarbonyl
5-ethoxycarbonyl
6-ethoxycarbonyl
5-acetamido
6-acetamido
by reaction with "A", the 5-dimethylamino-N-(mZ-1,2,5-oxadiazolo[3,4-b]pyridin-6-yl)-1-naphthalene-sulfonamides below are obtained in which mZ is 5-methyl
6-methyl
5,6-dimethyl
5-trifluoromethyl
6-trifluoromethyl
5-bromo
6-bromo
5,6-dibromo
5-bromo-6-methyl
5-methyl-6-bromo
5-bromo-6-ethyl
5-ethyl-6-bromo
5-bromo-6-trifluoromethyl
5-trifluoromethyl-6-bromo
5-chloro
6-chloro
5-nitro
6-nitro
5-bromo-6-tert-butyl
5-tert-butyl-6-bromo
5-chloro-6-methyl
5-methyl-6-chloro
5-dimethylamino
6-dimethylamino
5-cyano
6-cyano
5-methoxycarbonyl
6-methoxycarbonyl
5-ethoxycarbonyl
6-ethoxycarbonyl
5-acetamido
6-acetamido.

Analogously, by reaction of 7-amino-1,2,5-thiadiazolo[3,4-b]pyridine with "A", 5-dimethyl-N-(1,2,5-thiadiazolo[3,4-b]pyridin-7-yl)-1-naphthalene-sulfonamide is obtained.

Analogously, from the following mZ-7-amino-1,2,5-thiadiazolo[3,4-b]pyridines in which mZ is 5-methyl
6-methyl
5,6-dimethyl
5-trifluoromethyl
6-trifluoromethyl
5-bromo
6-bromo
5,6-dibromo
5-bromo-6-methyl
6-methyl-6-bromo
5-bromo-6-ethyl
5-ethyl-6-bromo
5-bromo-6-trifluoromethyl
5-trifluoromethyl-6-bromo
5-chloro
6-chloro
5-nitro
6-nitro
5-bromo-6-tert-butyl
5-tert-butyl-6-bromo
5-chloro-6-methyl
5-methyl-6-chloro
5-dimethylamino
6-dimethylamino
5-cyano
6-cyano
5-methoxycarbonyl
6-methoxycarbonyl
5-ethoxycarbonyl
6-ethoxycarbonyl
5-acetamido
6-acetamido
by reaction with "A" the 5-dimethylamino-N-(mZ-1,2,5-thiadiazolo[3,4-b]pyridin-6-yl)-1-naphthalene-sulfonamides below are obtained in which mZ is 5-methyl
6-methyl
5,6-dimethyl
5-trifluoromethyl
6-trifluoromethyl
5-bromo
6-bromo
5,6-dibromo
5-bromo-6-methyl 5-methyl-6-bromo
5-bromo-6-ethyl
5-ethyl-6-bromo
5-bromo-6-trifluoromethyl
5-trifluoromethyl-6-bromo
5-chloro
6-chloro
5-nitro
6-nitro
5-bromo-6-tert-butyl
5-tert-butyl-6-bromo
5-chloro-6-methyl
5-methyl-6-chloro
5-dimethylamino
6-dimethylamino
5-cyano
5-cyano
5-methoxycarbonyl
6-methoxycarbonyl
5-ethoxycarbonyl
6-ethoxycarbonyl
5-acetamido
6-acetamido.

Example 7

Analogously to Example 1, by reaction of 4-amino-2,1,3-benzoxadiazole with "A", 5-dimethylamino-N-(2,1,3-benzoxadiazol-4-yl)-1-naphthalenesulfonamide is obtained, and from the following 4-amino-mZ-2,1,3-benzoxadiazoles in which mZ is 5-methyl
6-methyl
7-methyl
5,6-dimethyl
5,7-dimethyl
6,7-dimethyl
5-trifluoromethyl
6-trifluoromethyl
7-trifluoromethyl
5-bromo
6-bromo
7-bromo
5,6-dibromo
5,7-dibromo
6,7-dibromo
5-bromo-6-methyl
5-bromo-7-methyl
6-bromo-7-methyl
5-methyl-6-bromo
5-methyl-7-bromo
6-methyl-7-bromo
5-bromo-6-ethyl
5-bromo-7-ethyl
6-bromo-7-ethyl
5-ethyl-6-bromo
5-ethyl-7-bromo
6-ethyl-7-bromo
5-bromo-6-trifluoromethyl
5-bromo-7-trifluoromethyl
6-bromo-7-trifluoromethyl
5-trifluoromethyl-6-bromo
5-trifluoromethyl-7-bromo
6-trifluoromethyl-7-bromo
5-chloro
6-chloro
7-chloro
5-nitro
6-nitro
7-nitro
5-bromo-6-tert-butyl
5-bromo-7-tert-butyl
6-bromo-7-tert-butyl
5-tert-butyl-6-bromo
5-tert-butyl-7-bromo
6-tert-butyl-7-bromo
5-chloro-6-methyl
5-chloro-7-methyl
6-chloro-7-methyl
5-methyl-6-chloro
5-methyl-7-chloro
6-methyl-7-chloro
5-dimethylamino
6-dimethylamino
7-dimethylamino
5-cyano
6-cyano
7-cyano
5-methoxycarbonyl
6-methoxycarbonyl
7-methoxycarbonyl
5-ethoxycarbonyl
6-ethoxycarbonyl
7-ethoxycarbonyl
5-acetamido
6-acetamido
7-acetamido with "A", the 5-dimethylamino-mZ-1-naphthalenesulfonamides below are obtained in which mZ is N-(5-methyl-2,1,3-benzoxadiazol-4-yl)
N-(6-methyl-2,1,3-benzoxadiazol-4-yl)
N-(7-methyl-2,1,3-benzoxadiazol-4-yl)
N-(5,6-dimethyl-2,1,3-benzoxadiazol-4-yl)
N-(5,7-dimethyl-2,1,3-benzoxadiazol-4-yl)
N-(6,7-dimethyl-2,1,3-benzoxadiazol-4-yl)
N-(5-trifluoromethyl-2,1,3-benzoxadiazol-4-yl)
N-(6-trifluoromethyl-2,1,3-benzoxadiazol-4-yl)
N-(7-trifluoromethyl-2,1,3-benzoxadiazol-4-yl)
N-(5-bromo-2,1,3-benzoxadiazol-4-yl)
N-(6-bromo-2,1,3-benzoxadiazol-4-yl)
N-(7-bromo-2,1,3-benzoxadiazol-4-yl)
N-(5,6-dibromo-2,1,3-benzoxadiazol-4-yl)
N-(5,7-dibromo-2,1,3-benzoxadiazol-4-yl)
N-(6,7-dibromo-2,1,3-benzoxadiazol-4-yl)
N-(5-bromo-6-methyl-2,1,3-benzoxadiazol-4-yl)
N-(5-bromo-7-methyl-2,1,3-benzoxadiazol-4-yl)
N-(6-bromo-7-methyl-2,1,3-benzoxadiazol-4-yl),
N-(5-methyl-6-bromo-2,1,3-benzoxadiazol-4-yl)
N-(5-methyl-7-bromo-2,1,3-benzoxadiazol-4-yl)
N-(6-methyl-7-bromo-2,1,3-benzoxadiazol-4-yl)
N-(5-bromo-6-ethyl-2,1,3-benzoxadiazol-4-yl)
N-(5-bromo-7-ethyl-2,1,3-benzoxadiazol-4-yl)
N-(6-bromo-7-ethyl-2,1,3-benzoxadiazol-4-yl)
N-(5-ethyl-6-bromo-2,1,3-benzoxadiazol-4-yl)
N-(5-ethyl-7-bromo-2,1,3-benzoxadiazol-4-yl)
N-(6-ethyl-7-bromo-2,1,3-benzoxadiazol-4-yl)
N-(5-bromo-6-trifluoromethyl-2,1,3-benzoxadiazol-4-yl)
N-(5-bromo-7-trifluoromethyl-2,1,3-benzoxadiazol-4-yl)
N-(6-bromo-7-trifluoromethyl-2,1,3-benzoxadiazol-4-yl)
N-(5-trifluoromethyl-6-bromo-2,1,3-benzoxadiazol-4-yl)
N-(5-trifluoromethyl-7-bromo-2,1,3-benzoxadiazol-4-yl)
N-(6-trifluoromethyl-7-bromo-2,1,3-benzoxadiazol-4-yl)
N-(5-chloro-2,1,3-benzoxadiazol-4-yl)

N-(6-chloro-2,1,3-benzoxadiazol-4-yl)
N-(7-chloro-2,1,3-benzoxadiazol-4-yl)
N-(5-nitro-2,1,3-benzoxadiazol-4-yl)
N-(6-nitro-2,1,3-benzoxadiazol-4-yl)
N-(7-nitro-2,1,3-benzoxadiazol-4-yl)
N-(5-bromo-6-tert-butyl-2,1,3-benzoxadiazol-4-yl)
N-(5-bromo-7-tert-butyl-2,1,3-benzoxadiazol-4-yl)
N-(6-bromo-7-tert-butyl-2,1,3-benzoxadiazol-4-yl)
N-(5-tert-butyl-6-bromo-2,1,3-benzoxadiazol-4-yl)
N-(5-tert-butyl-7-bromo-2,1,3-benzoxadiazol-4-yl)
N-(6-tert-butyl-7-bromo-2,1,3-benzoxadiazol-4-yl)
N-(5-chloro-6-methyl-2,1,3-benzoxadiazol-4-yl)
N-(5-chloro-7-methyl-2,1,3-benzoxadiazol-4-yl)
N-(6-chloro-7-methyl-2,1,3-benzoxadiazol-4-yl)
N-(5-methyl-6-chloro-2,1,3-benzoxadiazol-4-yl)
N-(5-methyl-7-chloro-2,1,3-benzoxadiazol-4-yl)
N-(6-methyl-7-chloro-2,1,3-benzoxadiazol-4-yl)
N-(5-dimethylamino-2,1,3-benzoxadiazol-4-yl)
N-(6-dimethylamino-2,1,3-benzoxadiazol-4-yl)
N-(7-dimethylamino-2,1,3-benzoxadiazol-4-yl)
N-(5-cyano-2,1,3-benzoxadiazol-4-yl)
N-(6-cyano-2,1,3-benzoxadiazol-4-yl)
N-(7-cyano-2,1,3-benzoxadiazol-4-yl)
N-(5-methoxycarbonyl-2,1,3-benzoxadiazol-4-yl)
N-(6-methoxycarbonyl-2,1,3-benzoxadiazol-4-yl)
N-(7-methoxycarbonyl-2,1,3-benzoxadiazol-4-yl)
N-(5-ethoxycarbonyl-2,1,3-benzoxadiazol-4-yl)
N-(6-ethoxycarbonyl-2,1,3-benzoxadiazol-4-yl)
N-(7-ethoxycarbonyl-2,1,3-benzoxadiazol-4-yl)
N-(5-acetamido-2,1,3-benzoxadiazol-4-yl)
N-(6-acetamido-2,1,3-benzoxadiazol-4-yl)
N-(7-acetamido-2,1,3-benzoxadiazol-4-yl).

Example 8

A mixture of 4.6 g of 5-dimethylamino-N-(5-bromo-6-ethyl-2,1,3-benzoxadiazol-4-yl)-1-naphthalenesulfonamide and 1.3 g of copper cyanide is heated for 8 hours at 120° in 30 ml of pyridine. The mixture is poured onto aqueous ammonia solution, worked up in the customary manner and 5-dimethylamino- N-(5-cyano-6-ethyl-2,1,3-benzoxadiazol-4-yl)-1-naphthalenesulfonamide is obtained.

Example 9

A solution of 1 g of 5-dimethylamino-N-(5-cyano-6-ethyl-2,1,3-benzoxadiazol-4-yl)-1-naphthalenesulfonamide and 0.7 g of potassium hydroxide in 20 ml of ethanol and 5 ml of water is boiled with stirring for 8 hours. The solvents are removed, the residue is dissolved in water and treated with hydrochloric acid and 5-dimethylamino-N-(5-carboxy-6-ethyl-2,1,3-benzoxadiazol-4-yl)-1-naphthalenesulfonamide is obtained.

Example 10

A solution of 1 g of 5-dimethylamino-N-(5-carboxy-6-ethyl-2,1,3-benzoxadiazol-4-yl)-1-naphthalenesulfonamide, 0.5 ml of conc. sulfuric acid and 30 ml of ethanol is heated for 6 hours at 80°. The solvent is removed, the residue is worked up in the customary manner and 5-dimethylamino-N-(5-ethoxy-carbonyl-6-ethyl-2,1,3-benzoxadiazol-4-yl)-1-naphthalenesulfonamide is obtained.

Example 11

A solution of 6 g of 4-amino-N-(2,1,3-benzothiadiazol-5-yl)-1-benzenesulfonamide and 0.5 g of titanium tetrachloride in 100 ml of methanol is treated with 1 ml of freshly distilled acetaldehyde. 4 g of sodium cyanoborohydride are then added thereto and the mixture is stirred for 30 hours. Cold half-concentrated hydrochloric acid is added thereto, the mixture is worked up in the customary manner and 4-ethylamino-N-(2,1,3-benzothiadiazol-5-yl)-1-benzenesulfonamide is obtained.

Example 12

A solution of 1 g of 4-isocyanato-N-(4-bromo-7-methyl-2,1,3-benzothiadiazol-5-yl)-1-benzenesulfonamide [obtainable by reaction of 4-bromo-5-amino-7-methyl-2,1,3-benzothiadiazole with 4-isocyanatobenzenesulfonyl chloride] in 80 ml of toluene is treated with 0.5 g of pyrrolidine and stirred for 1 hour at 90°. After customary working up, 4-pyrrolidinoamido-N-(4-bromo-7-methyl-2,1,3-benzothiadiazol-5-yl)-1-benzenesulfonamide is obtained.

Example 13

Analogously to Example 1, by reaction from the following M-naphthalene-sulfonylchlorides, in which M is 5-diethylamino
5-isopropylamino
5-isopropyl-methyl-amino
5-methylamino
5-ethylamino
5-propylamino
5-butylamino
5-pentylamino with 5-amino-2,1,3-benzothiadiazole, the M-N-2,1,3-benzothiadiazo-5-yl)-1-naphthalene sulfonamides below are obtained, in which M is 5-diethylamino
5-isopropylamino
5-isopropyl-methyl-amino
5-methylamino
5-ethylamino
5-propylamino
5-butylamino
5-pentylamino.

The following examples relate to pharmaceutical preparations:

Example A: Injection vials

A solution of 100 g of an active compound of the formula I and 5 g of disodium hydrogenphosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into moulds and allowed to cool. Each suppository contains 20 mg of active compound.

Example C: Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. The solution is adjusted to pH 6.8, made up to 1 l and sterilized by irradiation. This solution can be used in the form of eye drops.

Example D: Ointments 500 mg of an active compound of the formula I is mixed with 99.5 g of petroleum jelly under aseptic conditions.

Example E: Tablets

A mixture of 1 kg of active compound of the formula I, 4 kg of lactose, 1.2 kg of potato starch, 0.2 kg Of talc and 0.1 kg of magnesium stearate is compressed in a customary manner to give tablets such that each tablet contains 10 mg of active compound.

Example F: Coated tablets

Analogously to Example E, tablets are pressed which are then coated in a customary manner with a covering of sucrose, potato starch, talc, tragacanth and colorant.

Example G: Capsules 2 kg of active compound of the formula I are filled into hard gelatin capsules in a customary manner such that each capsule contains 20 mg of the active compound.

Example H: Ampoules

A solution of 1 kg of active compound of the formula I in 60 l of double-distilled water is sterile-filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula I

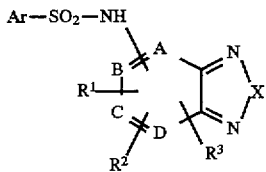

in which

—A=B—C=D— is a —CH=CH—CH=CH— group in which each H group can independently be replaced by $R^1$, $R^2$ or $R^3$, Ar is Ph or naphthyl, which is unsubstituted or mono-, di- or trisubstituted by H, Hal, Q, alkenyl having 2 to 6 C atoms, Ph, OPh, $NO_2$, $NR^4R^5$, $NHCOR^4$, $CF_3$, $OCF_3$, CN, $OR^4$, $COOR^4$, $(CH_2)_nCOOR^4$, —$(CH_2)_nNR^4R^5$, —N=C=O or $NHCONR^4R^5$, $R^1$, $R^2$ and $R^3$ are present only when 1–3 H groups in —A=B—C=D— are replaced thereby and, in each case independently of one another, are Hal, Q, $CF_3$, $NO_2$, $NR^4R^5$, CN, $COOR^4$ or $NHCOR^5$, $R^4$ and $R^5$ in each case independently of one another are H or Q, or together are also —$CH_2$—$(CH_2)_n$—$CH_2$—, Q is alkyl having 1 to 6 C atoms, Ph is phenyl, X is O or S, Hal is F, Cl, Br or I, n is 1, 2 or 3, and salts thereof, excluding the compounds 4-methyl-N-(2,1,3-benzothiadiazol-4-yl)benzenesulfonamide, 4-methyl-N-(2,1,3-benzothiadiazol-5-yl)benzene-sulfonamide, 4-nitro-N-(2,1,3-benzothiadiazol-5-yl)-benzenesulfonamide, 4-nitro-N-(2,1,3-benzothiadiazol-4-yl)benzenesufonamide, 4-amino-N-(2,1,3-benzothia-diazol-5-yl)benzenesulfonamide, and 4-amino-N-(2,1,3-benzothiadiazol-4-yl)-benzenesulfonamide.

2. A compound of claim 1, which compound is a) 5-bromo-2-ethyl-N-(2,1,3-benzothiadiazol-5-yl)benzene sulfonamide;

b) 2,5-dichloro-N-(2,1,3-benzothiadiazol-5-yl)benzene sulfonamide;

c) 5-bromo-2-propyl-N-(2,1,3-benzothiadiazol-5-yl)benzene sulfonamide;

d) 5-dimethylamino-N-(2,1,3-benzothiadiazol-5-yl)naphthalenesulfonamide;

e) 5-dimethylamino-N-[6-methyl-(2,1,3-benzothiadiazol-5-yl)]naphthalenesulfonamide;

f) 5-dimethylamino-N-[4-bromo-(2,1,3-benzothiadiazol-5-yl)]naphthalenesulfonamide;

g) 5-dimethylamino-N-(2,1,3-benzothiadiazol-4-yl)naphthalenesulfonamide;

h) 5-dimethylamino-N-(1,2,5-benzoxadiazol-5-yl)-1-naphthalenesulfonamide;

i) 5-dimethylamino-N-(6-bromo-7-methyl-1,2,5-benzoxadiazol-5-yl)-1-naphthalenesulfonamide; or j) 2-phenyl-N-(2,1,3-benzothiadiazol-5-yl)benzenesulfonamide.

3. A pharmaceutical composition comprising a compound of the formula I

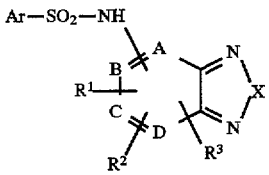

in which

—A=B—C=D— is a —CH=CH—CH=CH— group in which each H group can independently be replaced by $R^1$, $R^2$ or $R^3$, Ar is Ph or naphthyl, which is unsubstituted or mono-, di- or trisubstituted by H, Hal, Q, alkenyl having 2 to 6 C atoms, Ph, OPh, $NO_2$, $NR^4R^5$, $NHCOR^4$, $CF_3$, $OCF_3$, CN, $OR^4$, $COOR^4$, $(CH_2)_nCOOR^4$, —$(CH_2)_nNR^4R^5$, —N=C=O or $NHCONR^4R^5$, $R^1$, $R^2$ and $R^3$ are present only when 1–3 H groups in —A=B—C=D— are replaced thereby and, in each case independently of one another, are Hal, Q, $CF_3$, $NO_2$, $NR^4R^5$, CN, $COOR^4$ or $NHCOR^5$, $R^4$ and $R^5$ in each case independently of one another are H or Q, or together are also —$CH_2$—$(CH_2)_n$—$CH_2$—, Q is alkyl having 1 to 6 C atoms, Ph is phenyl, X is O or S, Hal is F, Cl, Br or I, n is 1, 2 or 3, or physiologically acceptable salts thereof, and at least one solid, liquid or semi-liquid excipient or auxiliary to provide the composition in a form suitable for pharmaceutical use.

4. A method for treating endothelin-dependent disorders comprising administering to a patient in need thereof, an endothelin receptor antagonist effective amount of a composition of claim 3.

5. A method for controlling cardiac, circulatory or vascular disorders comprising administering to a patient in need thereof an effective amount of a composition of claim 3.

6. A compound according to claim 1, wherein X is S.

7. A compound according to claim 1, wherein X is O.

8. A compound according to claim 1, wherein X is S and —A=B—C=D— is —CH=CH—CH=CH—.

9. A compound according to claim 1, wherein X is O and —A=B—C=D— is —CH=CH—CH=CH—.

10. A compound according to claim 1, wherein X is O and —A=B—C=D— is —CH=CH—CH=CH—, with two H groups replaced by $R^2$ and $R^3$ where $R^2$ is Hal and $R^3$ is methyl.

11. A compound according to claim 1, wherein Ar is 5-(N,N-dimethylamino)naphthyl.

12. The method of claim 4, wherein the compound of the formula I is administered in a daily dose of 0.02 to 10 mg/kg of body weight.

13. The method of claim 5, wherein the compound of the formula I is administered in a daily dose of 0.02 to 10 mg/kg of body weight.

* * * * *